United States Patent
Tamplin et al.

(10) Patent No.: US 11,883,436 B2
(45) Date of Patent: Jan. 30, 2024

(54) METHOD OF PREPARING HEMATOPOIETIC STEM AND PROGENITOR CELLS FOR TRANSPLANTATION

(71) Applicant: THE BOARD OF TRUSTEES OF THE UNIVERSITY OF ILLINOIS, Urbana, IL (US)

(72) Inventors: Owen James Tamplin, Middleton, WI (US); Kostandin Pajcini, Chicago, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 17 days.

(21) Appl. No.: 17/401,657

(22) Filed: Aug. 13, 2021

(65) Prior Publication Data
US 2022/0047639 A1   Feb. 17, 2022

Related U.S. Application Data

(60) Provisional application No. 63/068,736, filed on Aug. 21, 2020, provisional application No. 63/066,531, filed on Aug. 17, 2020.

(51) Int. Cl.
*A61K 35/28* (2015.01)
*C12N 5/0789* (2010.01)

(52) U.S. Cl.
CPC ............ *A61K 35/28* (2013.01); *C12N 5/0647* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 8,168,428 B2 | 5/2012 | Zon et al. | |
| 8,642,569 B2 | 2/2014 | Scadden et al. | |
| 9,527,828 B2 | 12/2016 | Nishino et al. | |
| 9,725,695 B2 | 8/2017 | Muotri et al. | |
| 9,834,755 B2 | 12/2017 | Bernstein et al. | |
| 2019/0359939 A1 | 11/2019 | Essen-Moller | |

OTHER PUBLICATIONS

Shao et al. The neurotransmitter receptor Gabbr1 regulates proliferation and function of hematopoietic stem and progenitor cells (2021) Blood, 137, pp. 775-787. (Year: 2021).*
Cutler et al. Prostaglandin-modulated umbilical cord blood hematopoietic stem cell transplantation (2013), Blood, 122, pp. 3074-3081. (Year: 2013).*
Seidel, J. et al. (2007) "The Neurotransmitter Gaba Is a Potent Inhibitor of the Stromal Cell-Derived Factor-1 Induced Migration of Adult CD133 Hematopoietic Stem and Progenitor Cells," Stem Cell Dev. 16(5):827-836.
Nestorowa, S., et al. (2016) "A single-cell resolution map of mouse hematopoietic stem and progenitor cell differentiation," Blood 128(8):e20-e31.
Olsson, A., et al. (2016) "Single-cell analysis of mixed-lineage states leading to a binary cell fate choice," Nature 537:698-702.
Seita, J., et al. (2012) "Gene Expression Commons: An Open Platform for Absolute Gene Expression Profiling," PLoS One 7(7):e40321.
Tajer, P., et al. (2019) "Ex Vivo Expansion of Hematopoietic Stem Cells for Therapeutic Purposes: Lessons from Development and the Niche," Cells 8(2):169.
Weinreb, C., et al. (2018) "SPRING: a kinetic interface for visualizing high dimensional single-cell expression data," Bioinformatics 34(7):1246-1248.
Zhu, F., et al. (2019) "The GABA receptor GABRR1 is expressed on and functional in hematopoietic stem cells and megakaryocyte progenitors," Proc. Natl. Acad. Sci. USA 116(37):18416-18422.

* cited by examiner

*Primary Examiner* — Kara D Johnson
*Assistant Examiner* — Maytee Marie Contes De Jesus
(74) *Attorney, Agent, or Firm* — LICATA & TYRRELL P.C.

(57) ABSTRACT

Disclosed are methods of preparing hematopoietic stem cells and progenitor cells (HSPCs) for transplant into a subject and to methods of using the treated cells. More particularly, methods of the invention comprise treating HSPCs ex vivo with an effective amount of a GABBR1 agonist and administering the treated HSPCs to the subject.

9 Claims, 3 Drawing Sheets

Specification includes a Sequence Listing.

METHOD OF PREPARING HEMATOPOIETIC STEM AND PROGENITOR CELLS FOR TRANSPLANTATION

INTRODUCTION

This application claims the benefit of priority from U.S. Provisional Application Ser. No. 63/066,531, filed Aug. 17, 2020, and 63/068,736, filed Aug. 21, 2020, the contents of which are incorporated herein by reference in their entireties.

This invention was made with government support under grant nos. HL134971, HL142998, DK103908, and DK106846 awarded by the National Institutes of Health. The government has certain rights in this invention.

BACKGROUND

Hematopoietic stem cell (HSCs) transplantation is a curative treatment for many blood diseases and cancers. However, the outcomes can be poor because transplanted HSCs fail to quickly and efficiently reconstitute the patient's immune system. An additional challenge is that it can be difficult to find an immune-matched donor. One option is to use umbilical cord blood (UCB) HSCs, because they are easier to match than adult HSCs. The disadvantage of UBC HSCs is that these cells are not abundant, and it can be difficult to purify enough for an adult transplant recipient. To overcome these obstacles in the clinic, researchers have sought different approaches to expand the number of UCB HSCs ex vivo prior to transplant. Currently, the favored approach is to treat UCB HSCs with small molecules for a brief period between collection and transplantation.

Small molecules have been identified that can expand UCB $CD34^+$ numbers before transplantation (Tajer, et al. (2019) Cells 8(2):169). However, these compounds have either limited improvement in HSPC engraftment (e.g., PGE2; North, et al. (2007) Nature 447(7147):1007-1011; US 2009/0285786 A1), lineage skewing (e.g., SR1; Wagner, et al. (2016) Cell Stem Cell 18:144-155), or require many days of culture (e.g., UM171; Fares, et al. (2014) Science 345(6203):1509-1512; U.S. Pat. No. 10,336,747 B2).

Therefore, there is a need in the art for methods that can increase the efficiency of hematopoietic stem and progenitor cell engraftment in the bone marrow to expand the applicability of hematopoietic stem cell transplantation and increase its success. The present invention provides a solution to these problems and further provides other uses and advantages that will be apparent to those skilled in the art.

SUMMARY OF THE INVENTION

This invention provides a method of preparing hematopoietic stem and progenitor cells (HSPCs) for transplant into a subject in need thereof by treating the HSPCs (e.g., $CD34^+$ HSPCs or umbilical cord blood HSPCs) ex vivo with an effective amount of a GABA B receptor (GABBR) modulator. In some aspects, the GABBR modulator is baclofen, saclofen, or 2-hydroxy-saclofen, or preferably a GABBR1 receptor agonist such as baclofen. In other aspects, the HSPCs are treated with the effective amount of the GABBR modulator (e.g., 1 nanomolar to about 50 micromolar) for about one to about 16 hours. In particular aspects, the HSPCs are treated with 10 micromolar baclofen for about 2 hours. A composition including the treated HSPCs in admixture with a carrier is also provided as is a method of using the same in a method of enhancing hematopoietic cell engraftment in a subject, wherein in some aspects, the treated HSPCs are administered systemically or locally.

DETAILED DESCRIPTION OF THE INVENTION

Figure 1:
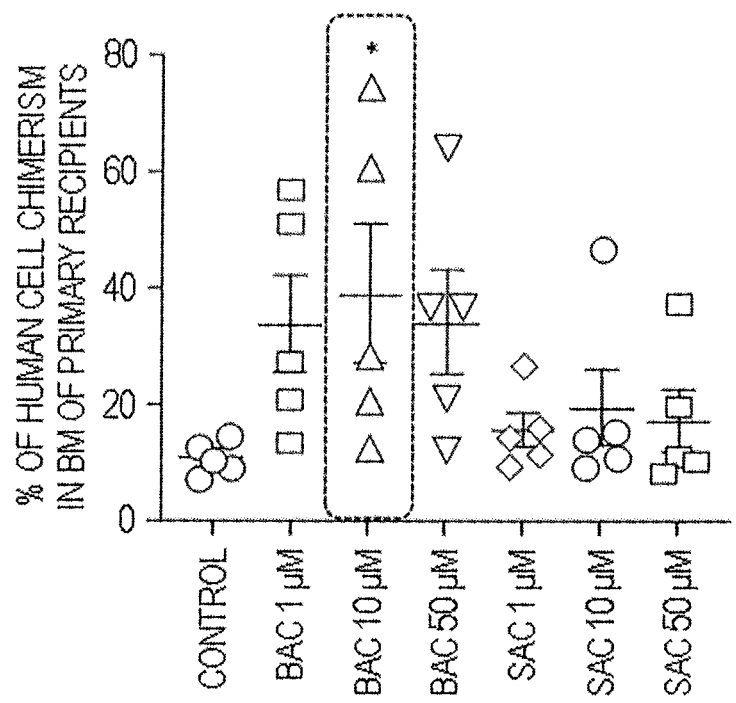
FIG. 1 show percent engraftment of human $CD45^+$ hematopoietic stem and progenitor cells in mouse recipients 16 weeks post-transplant. Prior to transplant, cells were treated ex vivo for 2 hours at 37° C. in media with GABA B Receptor 1 (GABBR1) agonist (Baclofen; "Bac") or antagonist (hydroxy-Saclofen; "Sac").

It has now been found that the neurotransmitter GABA regulates proliferation of hematopoietic stem and progenitor cells (HSPCs) and differentiation of B lineage cells. A subset of human and mouse HSPCs express GABA B receptor 1 (GABBR1). Notably, mice deficient for GABBR1 have defective HSPCs. By comparison, a brief ex vivo treatment of human $CD34^+$ HSPCs with a GABBR1 agonist, prior to xenotransplant in immuno-deficient mice, resulted in dramatically increased and sustained engraftment up to 16 weeks post-transplant. These results indicate the clinical application for the ex vivo treatment of umbilical cord blood (UCB) $CD34^+$ cells prior to transplant. In particular, a brief (2 hour) treatment of UCB $CD34^+$ cells with a 10 µM dose of GABBR1 agonist Baclofen before transplantation results in long-term engraftment with high chimerism. Specifically, chimerism was 2- to 8-fold higher, which is on par or better than Prostaglandin E2 (PGE2) that produces a 2- to 4-fold improvement in long-term engraftment (Cutler, et al. (2013) Blood 122(17):3074-81; Goessling, et al. (2011) Cell Stem Cell. 8(4):445-58; Goessling, et al. (2009) Cell 136(6):1136-47; North, et al. (2007) Nature 447(7147):1007-11). Accordingly, this invention provides a method of preparing HSPCs for transplant into a subject in need of such treatment by treating the HSPCs ex vivo with an effective amount of a GABA B receptor (GABBR) modulator. Further, the invention provides superior hematopoietic stem and progenitor cell preparations with increased engraftment/engraftment potential and/or increased proliferation.

A "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are sub-classified according to their developmental potential as totipotent, pluripotent, multipotent and oligo/unipotent. A "progenitor cell" also has the capacity to self-renew and to differentiate into more mature cells, but is committed to a lineage (e.g., hematopoietic progenitors are committed to the blood lineage; myeloid progenitors are committed to the myeloid lineage; lymphoid progenitors are committed to the lymphoid lineage), whereas stem cells are not necessarily so limited. "Self-renewal" refers a cell with a unique capacity to produce unaltered daughter cells and therefore replenish and maintain its population numbers, and to generate specialized cell types (potency). Self-renewal can be achieved in two ways. Asymmetric cell division produces one daughter cell that is identical to the parental cell and one daughter cell that is different from the parental cell and is a more committed progenitor or differentiated cell. Symmetric cell division produces two identical daughter cells. "Proliferation" or "expansion" of cells refers to symmetrically dividing cells.

Hematopoietic stem cells (HSGs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See U.S. Pat. Nos. 5,635,387; 5,460,964; 5,677,136; 5,750,397; 5,759,793; 5,681,599; 5,716,827). Hematopoietic stem cells have the ability to regenerate long-term multi-lineage hematopoiesis (e.g., "long-term engraftment") in individuals receiving a bone marrow or cord blood transplant. When transplanted into lethally irradiated animals or humans, hematopoietic stem cells can repopulate the erythroid, neutrophil-macrophage, megakaryocyte and lymphoid hematopoietic cell pool.

HSCs may be identified according to certain phenotypic or genotypic markers. For example, HSCs may be identified by their small size, lack of lineage (lin) markers, low staining (side population) with vital dyes such as rhodamine 123 (rhodamine$^{DULL}$, also called rho$^{lo}$) or Hoechst 33342, and presence of various antigenic markers on their surface, many of which belong to the cluster of differentiation series (e.g., CD34, CD38, CD90, CD133, CD105, CD45, and c-kit, the receptor for stem cell factor). HSCs are mainly negative for the markers that are typically used to detect lineage commitment, and, thus, are often referred to as Lin(−) cells. Most human HSCs may be characterized as CD34$^+$, CD59$^+$, Thy1/CD90$^+$, CD38$^{lo/−}$, C-kit/CD117$^+$, and Lin(−). However, not all stem cells are covered by these combinations, as certain HSCs are CD34$^−$/CD38$^−$. Also, some studies suggest that the earliest stem cells may lack c-kit on the cell surface. For human HSCs, CD133 may represent an early marker, as both CD34$^+$ and CD34$^−$ HSCs have been shown to be CD133$^+$. It is known in the art that CD34$^+$ and Lin(−) cells also include hematopoietic progenitor cells.

Suitable sources of hematopoietic stem and progenitor cells for use in the methods of the present invention include, but are not limited to, cells isolated or obtained from an organ of the body containing cells of hematopoietic origin. By "isolated" is meant material that is removed from its original environment. For example, a cell is isolated if it is separated from some or all of the components that normally accompany it in its native state. For example, an "isolated population of cells," an "isolated source of cells," or "isolated hematopoietic stem and progenitor cells" and the like, as used herein, refer to in vitro or ex vivo separation of one or more cells from their natural cellular environment, and from association with other components of the tissue or organ, i.e., it is not significantly associated with in vivo substances.

Hematopoietic stem and progenitor cells can be obtained or isolated from unfractionated or fractioned bone marrow of adults, which includes femurs, hip, ribs, sternum, and other bones. Hematopoietic stem and progenitor cells can be obtained or isolated directly by removal from the hip using a needle and syringe, or from the blood, often following pre-treatment with cytokines, such as G-CSF (granulocyte colony-stimulating factors), that induce cells to be released or mobilized from the bone marrow compartment. Other sources of hematopoietic stem and progenitor cells include umbilical cord blood, placental blood, peripheral blood, mobilized peripheral blood and a stem cell line. For experimental purposes, fetal liver, fetal spleen, kidney marrow, and AGM (Aorta-gonad-mesonephros) of animals are also useful sources of hematopoietic stem and progenitor cells. If the cells used are derived from an immortalized stem cell line, further advantages would be realized in the ease of obtaining and preparation of cells in adequate quantities.

In particular aspects, the hematopoietic stem or progenitor cells are harvested from a hematopoietic source, e.g., bone marrow cells, umbilical cord blood, or mobilized peripheral blood cells. "Harvesting" hematopoietic stem and progenitor cells is defined as the dislodging or separation of cells from the matrix. This can be accomplished using a number of methods, such as enzymatic, non-enzymatic, centrifugal, electrical, or size-based methods, or preferably, by flushing the cells using media (e.g., media in which the cells are incubated). In particular aspects, harvesting a sufficient quantity of cells for transplantation may require mobilizing the stem and progenitor cells in the donor.

Hematopoietic stem and progenitor cells of the invention can also be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the terms "reprogramming" refers to a method of increasing the potency of a cell to a less differentiated state. As used herein, the term "programming" refers to a method of decreasing the potency of a cell or differentiating the cell to a more differentiated state.

Hematopoietic stem and progenitor cells for use in the methods of the present invention may be depleted of mature hematopoietic cells such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD19, CD56, CD123, and CD235a. A subsequent step can be performed to further purify the population of cells, in which a substrate labeled with antibodies that bind to the $CD34^+$ antigen are used to isolate primitive hematopoietic stem and progenitor cells. Kits are commercially available for purifying hematopoietic stem and progenitor cells from various cell sources and in particular aspects, these kits are suitable for use with the methods of the present invention. Exemplary commercially available kits for purifying hematopoietic stem and progenitor cells include, but are not limited to Lineage (Lin) Depletion Kit (Miltenyi Biotec); $CD34^+$ enrichment kit (Miltenyi Biotec); Human T Cell Enrichment Cocktail sold under the tradename RosettaSep™ (Stem Cell Technologies).

The population of cells of the composition of the invention, in some aspects, has less than about 30%, 25%, 20%, 15%, 10% or 5% mesenchymal stem cells. In particular aspects, the population of cells has no more than about 10% mesenchymal stem cells. Mesenchymal stem cells (MSCs) are multipotent stem cells that can differentiate readily into lineages including osteoblasts, myocytes, chondrocytes, and adipocytes (Pittenger, et al. (1999) *Science* 284:143; Haynesworth, et al. (1992) *Bone* 13:69; Prockop (1997) *Science* 276:71).

In other aspects, the population of cells including the therapeutic composition of the invention has less than about 30%, 25%, 20%, 15%, 10% or 5% endothelial progenitor cells. In other aspects, the population of cells has less than about 10% endothelial progenitor cells. As used herein, "endothelial progenitor cell" refers to a multipotent or unipotent cell with the potential to differentiate into vascular endothelial cells.

In more particular aspects, the population of cells has no more than about 10% mesenchymal stem cells or endothelial progenitor cells.

The population of cells as obtained from a donor, or as otherwise provided, may be substantially free of mesenchymal stem cells and/or endothelial progenitor cells, and in particular aspects has less than about 10% mesenchymal stem cells and less than about 10% endothelial progenitor cells. The population of cells may alternatively be depleted of mesenchymal stem cells and/or endothelial progenitor cells using methods known in the art, for example, using immunomagnetic selection techniques, fluorescence-activated cell sorting, or a combination therein. The depletion methods can further include the use of at least one antibody specific for at least one of the cell-surface markers described herein.

In some aspects, the population of cells is depleted of endothelial progenitor cells, including cells positive for the CD14 cell surface marker and negative for CD45 ($CD14^+$/$CD45^-$) and/or cells positive for VWF (Von Willebrand Factor) ($VWF^+$). In other embodiments, the cell population is depleted of cells positive for CD73 and/or CD140B cell surface markers. In particular aspects of the invention, the population of cells includes cells positive for the cell surface marker CD34, and has less than about 30%, 25%, 20%, 15%, 10% or 5% of cells positive for a cell surface marker selected from the group of CD73, CD140B, CD14 and VWF.

In particular aspects, the population of cells of the composition of the invention includes $CD34^+$ cells and has less than about 30%, 25%, 20%, 15%, 10% or 5% $CD14^+$/$CD45^-$ cells. In other aspects of the invention, the population of cells includes $CD34^+$ cells and has less than about 30%, 25%, 20%, 15%, 10% or 5% $VWF^+$ cells. In other aspects of the invention, the population of cells includes $CD34^+$ cells and has less than about 30%, 25%, 20%, 15%, 10% or 5% $CD140B^+$ cells.

Hematopoietic stem and/or progenitor cells, whether obtained from cord blood, bone marrow, peripheral blood, or other source, may be grown, treated or expanded in any suitable, commercially available or custom defined medium, with or without serum, as desired (see, e.g., Hartshorn et al. (2007) *Cell Technology for Cell Products*, pages 221-224, R. Smith, Editor; Springer Netherlands). For instance, in certain aspects, serum-free medium may use albumin and/or transferrin, which have been shown to be useful for the growth and expansion of $CD34^+$ cells in serum-free medium. Also, cytokines may be included, such as Flt-3 ligand, stem cell factor (SCF), and thrombopoietin (TPO), among others. HSCs may also be grown in vessels such as bioreactors (see, e.g., Liu, et al. (2006) *J. Biotechnol.* 124:592-601). A suitable medium for ex vivo expansion of HSCs may also include HSC supporting cells, such as stromal cells (e.g., lymphoreticular stromal cells), which can be derived, for instance, from the disaggregation of lymphoid tissue, and which have been shown to support the in vitro, ex vivo, and in vivo maintenance, growth, and differentiation of HSCs, as well as their progeny.

"Expansion" or "expanded" in the context of cells refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells.

In some aspects, the population of cells is not expanded ex vivo or in vitro prior to administration to a subject. In particular aspects, an unexpanded population of cells is obtained, the population of cells is treated ex vivo in accordance with the protocol provided herein, may be washed to remove the treatment agent, and administered to a subject without expansion of the cell population ex vivo. In some aspects, cells are obtained from a donor, including cord blood, and are not expanded prior to or after treatment of the cells, or at any time prior to administration of the therapeutic composition to a subject. In one aspect, an unexpanded population of cells is treated and is administered to a subject prior to any substantial ex vivo cell division of the cells in the population, or prior to the time required for any substantial cell division ex vivo. In other aspects, an unexpanded population of cells is treated and is administered to a subject prior to any substantial ex vivo mitosis of the cells in the population, or prior to the time required for any substantial mitosis ex vivo. In some aspects, an unexpanded population of cells is treated and is administered to a subject prior to the doubling time of the cells in the population. In some aspects, an unexpanded population of cells is treated and is administered to a subject within 6, 12, or 24 hours of treatment of the cells. In other embodiments, an unexpanded population of cells is treated and is administered to a subject within 2 hours of treatment of the cells.

In various aspects, the population of cells is not cultured prior to treatment with a GABBR modulator ex vivo or at any time prior to administration to a subject. In some embodiments, the population of cells is cultured for less than about 24 hours. In other embodiments, the population of cells is cultured for less than about 12 hours, 10 hours, 8 hours, 6 hours, 4 hours, or two hours.

In various aspects, the population of cells that is treated with a GABBR modulator as described elsewhere herein and subsequently administered to a subject is a heterogeneous population of cells including, whole bone marrow, umbilical cord blood, mobilized peripheral blood, hematopoietic stem cells, hematopoietic progenitor cells, and the progeny of hematopoietic stem and progenitor cells, including granulocytes (e.g., promyelocytes, myelocytes, metamyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages).

A composition of this invention may include a cell population that is about 100% hematopoietic stem and progenitor cells. Alternatively, the population of cells in the composition is less than about 0.1%, 0.5%, 1%, 2%, 5%, 10%, 15%, 20%, 25%, or 30% hematopoietic stem and progenitor cells. Optionally, the population of cells is less than about 0.1%, 0.5%, 1%, 2%, 5%, 10%, 15%, 20%, 25%, or 30% CD34$^+$ cells. In other aspects, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% hematopoietic stem and progenitor cells. In particular aspects, the population of cells is about 0.1%-1%, about 1%-3%, about 3%-5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% CD34$^+$ cells.

In some aspects, the present invention provides a composition, e.g., a therapeutic composition composed of a population of cells for use in a transplant, for example, a bone marrow transplant, in admixture with a carrier. As used herein, the terms "population of cells" refers to a heterogeneous or homogenous population of cells composed of hematopoietic stem and/or progenitor cells. The population of cells composed of hematopoietic stem and/or progenitor cells may be bone marrow cells, umbilical cord blood cells, or mobilized peripheral blood cells, or a population of cells obtained from any suitable source, including bone marrow, mobilized peripheral blood, and umbilical cord blood among others. The term "collection of cells" also refers to a population of cells, and in some aspects is synonymous with "population of cells." However, a collection of cells need not refer to the any particular population of cells.

Cells in the composition of the invention can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In particular aspects, the cells of the invention are allogeneic.

HSPCs maintain hematopoiesis throughout life by self-renewal or multi-lineage differentiation to produce mature progeny. The BM serves as the HSPC microenvironment niche, where HSPCs receive signals regulating their proliferation, differentiation, or quiescence. The nervous system innervates the BM niche, and regulates HSPCs during homeostasis and tissue regeneration. The nervous system indirectly regulates HSPCs by modulating BM niche stromal cells. However, there is also evidence for expression of neuroreceptors on HSPCs.

Gamma-aminobutyric acid (GABA) is the main inhibitory neurotransmitter in the central nervous system (CNS). It binds GABA A ligand-gated ion channel receptors, or GABA B G protein-coupled receptors. GABA is also found in peripheral tissues such as pancreas, spleen, and lung.

Using a CRISPR-generated global Gabbr1 knockout mouse model, it has now been demonstrated that Gabbr1 can regulate the HSPC pool. Gabbr1 null mice showed decreased HSPC BM numbers and peripheral lymphoid cell numbers. Cell colony assays indicated Gabbr1 null mice had few cycling progenitors. Significantly, Gabbr1 null HSPCs showed reduced proliferative ability and hematopoietic reconstitution. Expression profiling from Gabbr1 null HSPCs revealed significant deregulation of B cell differentiation. Additionally, human CD34+ umbilical cord blood (UBC) HSPCs treated with the GABBR1 agonist, baclofen, produced sustained increases in BM chimerism and progenitor numbers for up to 16 weeks in a xenograft mouse model. This indicates that neuroreceptor GABBR1 is a critical regulator of the HSPC pool.

Hematopoietic and nervous systems are linked via innervation of bone marrow (BM) niche cells. Hematopoietic stem/progenitor cells (HSPCs) express neurotransmitter receptors, such as the γ-aminobutyric acid (GABA) type B receptor subunit 1 (GABBR1), suggesting that HSPCs could be directly regulated by neurotransmitters like GABA that directly bind to GABBR1. Imaging mass spectrometry (IMS) was carried out and it was found that endogenous GABA molecule is regionally localized and concentrated near the endosteum of the BM niche. To better understand the role of GABBR1 in regulating HSPCs, a constitutive Gabbr1 knockout mouse model was generated. Analysis revealed that HSPC numbers were significantly reduced in the BM compared to wild-type littermates. Moreover, Gabbr1 null hematopoietic stem cells (HSCs) had diminished capacity to reconstitute irradiated recipients in a competitive transplantation model. Gabbr1 null HSPCs were less proliferative under steady-state conditions and upon stress. Colony assays demonstrated that almost all Gabbr1 null HSPCs were in a slow or non-cycling state. In vitro differentiation of Gabbr1 null HSPCs in co-cultures, produced fewer overall cell numbers with significant defects in differentiation and expansion of the B cell lineage. To determine if GABBR1 agonist could stimulate human umbilical cord blood (UCB) HSPCs, brief ex vivo treatment prior to transplant into immunodeficient mice was performed, with significant increases in long-term engraftment of HSPCs compared to GABBR1 antagonist or vehicle treatments. These results indicate a direct role for GABBR1 in HSPC proliferation, and identify a target to improve HSPC engraftment in clinical transplantation.

Based upon the data presented herein, hematopoietic stem and progenitor cells (HSPCs) are prepared for transplant into a subject by treating the HSPCs ex vivo with an effective amount of a GABA B receptor modulator. As used herein, "GABA B receptor modulator" refers to GABA B receptor agonists; GABA B receptor B partial agonists; GABA B receptor agonists that act as functional antagonist (by receptor internalization); GABA B receptor antagonist; and positive allosteric modulators (PAMs). Ideally, the GABA B receptor modulator acts on hematopoietic stem cell and progenitor cells (HSPCs) expressing the GABA B receptor to stimulate the HSPCs resulting in enhanced efficiency or rate of engraftment upon transplant of the treated HSPCs into a subject. In certain aspects, the GABA B receptor modulator is a GABA B receptor agonist. In particular aspects, the GABA B receptor modulator is a GABA B receptor 1 (GABBR1) agonist.

The effective amount of the GABA B modulator is preferably about 1 nanomolar to about 50 micromolar. In certain aspects, the effective amount of the GABA B agonist is about 1 nanomolar to about 50 micromolar. In other aspects, the effective amount of the GABA B agonist is about 0.005 micromolar, about 0.05 micromolar, about 0.5 micromolar, about 5 micromolar, about 10 micromolar, about 20 micromolar, about 30 micromolar, about 40 micromolar, or about 50 micromolar.

The HSPCs are treated with the GABA B receptor modulator for a period of about 1 to about 16 hours prior to engraftment. In certain aspects, the HSPCs are treated with the GABA B agonist for a period of about 1 hour to about 15 hours, about 1 hour to about 14 hours, about 1 hour to about 13 hours, about 1 hour to about 12 hours, about 1 hour to about 11 hours, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4 hours, about 1 hour to about 3 hours, or about 1 hour to about 2 hours prior to engraftment.

Examples of suitable GABA B receptor modulators include agonists such as baclofen, and antagonists such as 2-hydroxy-saclofen and saclofen. As used herein, baclofen refers to 4-amino-3-(4-chorophenyl)-butanoic acid or a pharmaceutically acceptable salt or ester thereof. Baclophen (sold under the tradenames KEMSTRO®, LIORESAL®, and GABLOFEN®) is an approved treatment for muscle spasms. Saclofen refers to 3-Amino-2-(4-chlorophenyl)propylsulfonic acid or a pharmaceutically acceptable salt or ester thereof. 2-Hydroxysaclofen refers to 3-Amino-2-(4-chlorophenyl)-2-hydroxypropyl-sulfonic acid or a pharmaceutically acceptable salt or ester thereof.

Additional GABA B receptor agonists include (3-amino-2(S)-hydroxypropyl)methylphosphinic acid (CGP 44532), 3-aminopropyl(methyl)phosphinic acid (SKF 97541), Lesogaberan (AZD-3355), 3-aminopropylphosphonic acid (3-APA), (3-amino-2-fluoropropyl)phosphinic acid; (2R)-(3-amino-2-fluoropropyl)phosphinic acid; (2S)-(3-amino-2-fluoropropyl)phosphinic acid; (3-amino-2-fluoro-1-methylpropyl)phosphinic acid; (3-amino-2-oxopropyl)phosphinic acid; (2S)-(3-amino-2-hydroxypropyl)phosphinic acid; (R)-(3-amino-2-hydroxypropyl)phosphinic acid; and (3-amino-1-fluoro-2-hydroxypropyl)phosphinic acid. Additional agonists include 4-aminobutanoic acid derivatives having different heterocyclic substituents on the 3-carbon of the butyl chain (see EP 463969 A1 and FR 2722192 A1); substituted 3-aminopropylphosphinic acid (see EP 181833 A1); and sulfinic acid analogs (see Carruthers, et al. (1998) *Bioorgan. Med. Chem. Lett.* 8(21):3059-3064). See also Froestl, et al. (1995) *J. Med. Chem.* 38:3297-3312; Kerr & Ong (2001) *Curr. Med. Chem.-Central Nervous System Agents* 1(1):27-42; and U.S. Pat. No. 8,344,028 B2, incorporated herein by reference in its entirety.

Agonists disclosed herein may be used alone or in combination with positive allosteric regulators that increase the potency and/or inherent efficacy of GABA B receptor agonists. Examples of positive allosteric regulators include, but are not limited to, 2,6-di-tert-butyl-4-(3-hydroxy-2,2-dimethylpropyl) phenol (CGP7930) and 3-(3,5-di-tert-butyl-4-hydroxyphenyl)-2,2-dimethylpropanal (see U.S. Pat. No. 5,304,685). In addition, N,N-dicyclopentyl-2-methylsulfanyl-5-nitro-pyrimidine-4,6-diamine has been described as positive allosteric regulator of the GABA B receptor (Urwyler, et al. (2003) *J. Pharmacol. Exp. Therapeut.* 307:322-330). Further, xantinine compounds as disclosed in WO 2008/130314 may be used as positive allosteric regulators. US 2006/0094754 A1 and WO 2009/041904 A1 also disclose the preparation of quinolines as allosteric enhancers of the GABA B receptor.

In certain aspects, the GABA B receptor modulator is a GABBR1 receptor agonist. In a particular aspects, the GABA B receptor modulator is baclofen. In another particular aspect, the effective amount of baclofen is about 10 micromolar. In another particular aspect, the HSPCs are treated with 10 micromolar baclofen for about 2 hours.

Treatment of hematopoietic stem and progenitor cells with a GABA B receptor modulator ideally modifies gene expression of the cells to improve the engraftment potential of said cells as compared to the same cells that have not received treatment with the GABA B receptor modulator. "Engraftment potential" refers to the ability of a cell to engraft. In particular aspects, the engraftment potential of a hematopoietic stem or progenitor cell, such as a CD34$^+$, Lin(–) cell, can be determined by measuring, for example, the expression in the cell of genes associated with engraftment, cell viability, and the capacity of the cell to self-renew ex vivo. Of course, the skilled artisan would appreciate other suitable ex vivo assays that would also indicate an increased engraftment potential in a hematopoietic stem or progenitor cell.

Subjects in need of the treated HSPCs of this invention include those having a disease of the hematopoietic system. Representative diseases of the hematopoietic system can include, but are not limited to, cancers (e.g., leukemia, lymphoma), blood disorders (e.g., inherited anemia, inborn errors of metabolism, aplastic anemia, beta-thalassemia, Blackfan-Diamond syndrome, globoid cell leukodystrophy, sickle cell anemia, severe combined immunodeficiency, X-linked lymphoproliferative syndrome, Wiskott-Aldrich syndrome, Hunter's syndrome, Hurler's syndrome Lesch Nyhan syndrome, osteopetrosis), chemotherapy rescue of the immune system, and other diseases (e.g., autoimmune diseases, diabetes, rheumatoid arthritis, system lupus erythromatosis).

Accordingly, in other aspects, this invention is a method of enhancing hematopoietic cell engraftment in a subject by treating hematopoietic stem and progenitor cells (HSPCs) ex vivo with an effective amount of a GABA B receptor modulator and administering the treated HSPCs to the subject. "Enhancing hematopoietic cell engraftment" refers to an increase in the efficiency or rate (i.e., amount of engraftment over a period of time) of hematopoietic stem and progenitor cells of at least 10% in individuals treated with HSPCs according to the invention compared to untreated individuals. Preferably the rate of hematopoietic cell engraftment is increased by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 500-fold, at least 1000-fold or higher in individuals being treated with HSPCs according to the invention compared to the efficiency/rate of engraftment in an untreated individual.

The term "engraftment" or "engraft" is used herein to refer to the ability of hematopoietic stem cells or progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic progenitor cells, or survival of a recipient. In one aspect, engraftment is determined by measuring white blood cell counts in peripheral blood during a post-transplant period. Alternatively, engraftment can be assessed by measuring recovery of marrow cells in a bone marrow aspirate sample.

As used herein, "subject" is meant an individual and includes, for example, domesticated animals, such as cats and dogs, livestock (e.g., cattle, horses, pigs, sheep, and goats), laboratory animals (e.g., mice, rabbits, rats, and guinea pigs) mammals, non-human mammals, primates, non-human primates, rodents, birds, reptiles, amphibians, fish, and any other animal. The subject is preferably a mammal such as a primate or a human.

As used herein, the terms "treat," "treating," "treatment," and the like refer to eliminating, reducing, relieving, reversing, and/or ameliorating a disease or condition and/or symptoms associated therewith, in this case treating diseases of the hematopoietic system.

Although not precluded, treating a disease or condition does not require that the disease, condition, or symptoms associated therewith be completely eliminated, including the treatment of acute or chronic signs, symptoms and/or malfunctions. "Treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. "Treatment" therefore also includes relapse prophylaxis or phase prophylaxis. The term "treat" and synonyms contemplate administering a therapeutically effective amount of the hematopoietic stem cells of the invention to an individual in need of such treatment. A treatment can be orientated symptomatically, for example, to suppress symptoms. Treatment can be carried out over a short period, be oriented over a medium term, or can be a long-term treatment, for example within the context of a maintenance therapy.

The terms "therapeutically effective amount" or "effective dose" as used herein refers to an amount of the active ingredient(s) that, when administered, is (are) sufficient, to efficaciously deliver the active ingredient(s) for the treatment of a condition or disease of interest to an individual in need thereof. The effective amount of hematopoietic stem cells of the invention in each individual case may be determined empirically by a skilled artisan according to established methods in the art. The amount of hematopoietic stem or progenitor cells contained in the composition and administered to a patient will vary with the source of the cells, disease state, age, sex, and weight of the individual, and the ability of the hematopoietic stem and progenitor cells to elicit a desired response in the individual. As used in the context of the invention, "administering" includes in vivo administration to an individual as well as administration directly to cells or tissue in vitro or ex vivo.

In one aspect, the amount of hematopoietic stem or progenitor cells in the composition administered to a subject is the amount of hematopoietic stem or progenitor cells in a partial or single cord of blood, or at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

Treated HSPCs according to the invention can be administered to a subject either locally or systemically. Methods for administering bone marrow transplants to a subject are known in the art and are described in medical textbooks, e.g., Whedon (1991) Whedon, M. B. "Bone Marrow Transplantation: Principles, Practice, and Nursing Insights", Boston:Jones and Bartlett Publishers. In certain aspects, bone marrow cells from a healthy subject can be removed, preserved, and then replicated and re-infused should the subject develop an illness which either destroys the bone marrow directly or whose treatment adversely affects the marrow. If the subject is receiving his or her own cells, this is called an autologous transplant; such a transplant has little likelihood of rejection.

Exemplary methods of administering stem cells to a subject, particularly a human subject, include injection or transplantation of the cells into target sites in the subject. The hematopoietic stem cells can be inserted into a delivery device which facilitates introduction, by injection or transplantation, of the cells into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, or alternatively embedded in a support matrix when contained in such a delivery device.

Support matrices in which the stem cells can be incorporated or embedded include matrices which are recipient-compatible and which degrade into products which are not harmful to the recipient. The support matrices can be natural (e.g., collagen, etc.) and/or synthetic biodegradable matrices. Synthetic biodegradable matrices include synthetic polymers such as polyanhydrides, polyorthoesters, and polylactic acid; see also, for example, U.S. Pat. Nos. 4,298,002 and 5,308,701.

While treated HSPCs may be used as is, in certain aspects, the cells are in admixture with a suitable carrier, e.g., a pharmaceutically or therapeutically acceptable carrier (additive) and/or diluent, prior to being transplanted into a subject in need of treatment. Pharmaceutically acceptable carriers and diluents include solvents, cell culture medium, dispersion media, and/or aqueous saline or buffer solutions such as phosphate buffered saline (PBS), Ringer's solution, 5% dextrose in water (D5W), or normal/physiologic saline (0.9% NaCl). The use of such carriers and diluents is known in the art. The composition is preferably sterile and fluid to the extent that easy syringability exists.

Preferably, the composition is stable under the conditions of manufacture and storage and preserved against the contaminating action of microorganisms such as bacteria and fungi through the use of preservatives, for example, parabens, chlorobutanol, phenol, ascorbic acid, thimerosal, and the like. Compositions of the invention can be prepared by incorporating stem cells as described herein in a pharmaceutically acceptable carrier or diluent and, as required, other ingredients enumerated above, followed by filtered sterilization.

The following non-limiting examples are provided to further illustrate the present invention.

Example 1: Materials and Methods

Mouse Strains. All mice were housed at University of Illinois Chicago (UIC) AAALAC-certified animal facilities. Food and water ad libitum were routinely given. The Institutional Animal Care and Use Committees of UIC approved all experimental procedures. C57/BL6 (CD45.2), CD45B6.SJL-Ptprc$^a$Pep3$^b$/BoyJ (CD45.1), and Rag1$^{-/-}$ mice (Mombaerts, et al. (1992) Cell 68(5):869-877) were purchased from Jackson Lab (Bar Harbor, ME) or Charles River (Wilmington, MA). CD45.1/2 were generated by crossing CD45.1 females with CD45.2 males. Gabbr1 C57/BL6 knockout (Gabbr1$^{-/-}$) mice were generated at the University of Chicago by CRISPR/Cas9 base pair insertion leading to a nonsense mutation. Postnatal day P13 and P15 Gabbr1$^{-/-}$ mice were used due to survival defects at postnatal-day 20 (P20) (Schuler, et al. (2001) Neuron 31(1):47-58; Prosser, et al. (2001) Mol. Cell. Neurosci. 17(6):1059-1070; Quéva, et al. (2003) Br. J. Pharmacol. 140(2):315-322).

Analysis of Hematopoietic Populations. After isolation and cellularization of bone marrow (BM) and fetal liver (FL) hematopoietic cells, antibody staining was performed, followed by flow cytometry (BD LSRFortessa™ Flow Cytometer). Details of the primary antibodies are in Table 1. The secondary antibody was Donkey anti-Mouse IgG Secondary Antibody conjugated to a fluorescent dye sold under the tradename ALEXA FLUOR® 488 (Invitrogen). Data were analyzed using BD FACSDiva™ 6.0 (BD Biosciences) and FlowJo software.

TABLE 1

| Markers | Clone | Antibody isotype | Conjugate |
|---|---|---|---|
| CD45R/B220[1] | RA3-6B2 | IgG$_{2a}$ | PE |
| CD45R/B220[1] | RA3-6B2 | IgG$_{2a}$ | Fluorescent dye sold under the tradename ALEXA FLUOR ®(AF) 700 |
| CD3[1] | 17A2 | IgG$_1$ | PE |
| CD11b[1] | M1/70 | IgG$_{2b}$ | PE |
| Gr-1[1] | RB6-8C5 | IgG$_{2b}$ | PE |
| Ter-119[1] | Ter-119 | IgG$_{2b}$ | PE |
| CD45R/B220[1] | RA3-6B2 | IgG$_{2a}$ | FITC |
| CD45R/B220[1] | RA3-6B2 | IgG$_{2a}$ | APC |
| CD3e[1] | 17A2 | IgG$_1$ | FITC |
| CD11b[1] | M1/70 | IgG$_{2b}$ | FITC |
| Gr-1[1] | RB6-8C5 | IgG$_{2b}$ | FITC |
| Ter-119[1] | Ter-119 | IgG$_{2b}$ | FITC |
| CD16/CD32[1] | 93 | IgG$_{2a}$ | purified |
| CD16/CD32[1] | 93 | IgG$_{2a}$ | PE-CY7 |
| CD34[1] | HM34 | IgG | PE |
| CD45.2[1] | 104 | IgG$_{2a}$ | AF 700 |
| CD45.1[1] | A20 | IgG$_{2a}$ | PerCP-Cy5.5 |
| CD43[1] | S11 | IgG$_{2b}$ | PerCP-Cy5.5 |
| CD24[1] | M1/69 | IgG$_{2b}$ | APC/Fire ™ 750 |
| Bp-1[1] | 6C3 | IgG$_{2a}$ | PE/Cyanine7 |
| IgM[1] | RMM-1 | IgG$_{2a}$ | APC |
| IgD[1] | 11-26c.2a | IgG$_{2a}$ | PE |
| Sca-1[1] | D7 | IgG$_{2a}$ | PerCP-Cy5.5 |
| c-kit[1] | 2B8 | IgG$_{2b}$ | APC-CY7 |
| CD150[1] | 9D1 | IgG$_{2a}$ | PE-CY7 |
| CD150[1] | TC15-12F12.2 | IgG$_{2a}$ | Brilliant Violet 605 ™ |
| CD48[1] | HM481 | IgG$_{2a}$ | APC |
| CD48[1] | HM481 | IgG$_{2a}$ | AF 700 |
| CD127[1] | A7R34 | IgG$_{2a}$ | APC |
| CD135[1] | A2F10 | IgG$_{2a}$ | PE |
| CD4[1] | GK1.5 | IgG$_{2b}$ | PE-CY7 |
| CD8[1] | 53-6.7 | IgG$_{2a}$ | APC-CY7 |
| Ki-67 | 16A8 | IgG$_{2a}$ | FITC |
| Annexin V1 | — | — | FITC |
| GAD1/GAD-67[2] | F-6 | IgG$_3$ | none |
| GABA$_B$ R1[2] | D-2 | IgG$_1$ | none |

[1]Biolegend; [2]Santa Cruz Biotechnology.

Noncompetitive Stem Cell Transplantation. BM cells (1×10$^6$) harvested from three pooled day 15 (P15) Gabbr1$^{+/+}$ or Gabbr1$^{-/-}$ littermate mice were transplanted into lethally-irradiated CD45.1 recipients. For hematopoietic stem cell (HSC) transplantation, 350 HSCs (Lin$^-$/Sca1$^+$/cKit$^+$/CD48$^-$/CD150$^+$ from BM of Gabbr1$^{+/+}$ or Gabbr1$^{-/-}$ mice were injected into irradiated CD45.1 recipients with 5×10$^5$ CD45.1/2 spleen cells. Recipients were maintained on antibiotic water for one week before, and two weeks after transplantation. Donor reconstitution was measured in peripheral blood (at 1, 2, 3 months, lysed with ACK (Ammonium-Chloride-Potassium) lysis buffer), and BM at 3 months. Antibodies included PercpCy5.5-conjugated-CD45.1, AF 700-conjugated-CD45.2, APC-conjugated-B220, FITC-conjugated-Gr-1, PE-conjugated-CD11b, PE-Cy7-conjugated-CD4, APC-Cy7-conjugated-CD8. See Table 1.

Competitive Transplantation. For primary competitive transplantation, 350 HSCs (Lin$^-$/Sca1$^-$/cKit$^+$/CD48$^-$/CD150$^+$) from 3-4 Gabbr1$^{+/+}$ or Gabbr1$^{-/-}$ littermates (CD45.2) were sorted and mixed with 350 competitor HSCs pooled from 3-4 CD45.1/2 wild-type mice. Mixed cells were retro-orbitally transplanted into lethally irradiated congenic CD45.1 recipients with 5×10$^5$ CD45.1 spleen cells. Donor reconstitution was evaluated as above. Secondary transplants followed.

Imaging Mass Spectrometry (IMS). Femurs were harvested from female 6- to 8-week-old C57/BL6 mice, frozen fresh in 2% carboxymethylcellulose (EMD Millipore) in pre-chilled hexane on dry ice and stored at −80° C. Bones were sectioned at 10 microns using MX35 blades (Thermo Scientific) on a Leica CM 1850 UV cryostat. Copper tape was adhered to the slides prior to collection and a roll plate was necessary to keep the samples from fracturing. After femurs were adhered to indium tin-oxide (ITO)-coated glass sides (Bruker Daltonics) using double-sided copper conductive tape (Electron Microscopy Sciences), the samples were prepared for matrix-assisted laser desorption/ionization (MALDI) time-of-flight (TOF) IMS. A 1:1 mixture of 2,5-dihydroxybenzoic acid (DHB (98%), Sigma) and α-cyano-4-hydroxycinnamic acid (CHCA (98%), Sigma) was applied via a HTX TM-Sprayer™. The solution for the sprayer was prepared as follows: 5 mg/mL of a 1:1 mixture of DHB and CHCA was dissolved in 90:10 ACN:H$_2$O+0.1% trifluoroacetic acid (TFA) and sonicated to ensure solubility. The matrix mixture was recrystallized as previously reported (Spiegel, et al. (2007) Nat. Immunol. 8(10):1123-1131). The following instrument parameters were used to apply the matrix: Flow rate=0.2 mL/min, Velocity=1100 mm/min, Temperature: 30° C., Track spacing=3 mm, Passes=8, Nitrogen Pressure=10 psi, Spray Pattern=CC, Drying time=0 sec, and Nozzle Height=40 mm. Matrix was only applied to areas of the slide with bone sample.

Phosphorus red was used as a calibrant; 0.5 μL of a mg/μL solution in MeOH was spotted onto the glass directly adjacent to the copper tape. Standards of γ-aminobutyric acid (GABA, Sigma) were spotted in the following concentrations directly onto areas of bone that were not selected for IMS analysis: 10 mM, 1 mM, 100 μM, 10 μM, and 1 μM. Each standard was dissolved in $H_2O$ and mixed with matrix (1:1 CHCA:DHB in 70:30 ACN:$H_2O$+0.1% TFA) in a 1:1 ratio and 1 μL of each was spotted. Once dry, the slide was scanned at 1200 dpi. Three sections across the four bone slices were imaged to represent one complete bone: 'top,' 'middle,' and 'bottom.' The regions that were most intact (i.e., not fractured during sectioning) were chosen for IMS, and data were acquired using flexControl v 3.4 at 20 μm spatial resolution on an AUTOFLEX® Speed LRF MALDI-TOF mass spectrometer (Bruker Scientific, Billerica, MA) over the mass range 40-700 Da. In positive reflectron mode, laser power was set to 40%, laser width to 3 and reflector gain to 10×. For each raster point, 500 laser shots at 2000 Hz were shot in a random walk method. Data were subsequently analyzed in flexImaging v 4.1×64 (Bruker Daltonics, Billerica, MA). All spectra were normalized to root mean square (RMS). SCiLS statistical analysis software (Bruker Daltonics) was used to validate that GABA is in significantly higher abundance in the endosteal region than in other regions of the bone, and the colocalization algorithm was employed to detect m/z's that were significantly correlated between the highest concentrations of GABA standard (10 mM and 1 mM, as the limit of detection sits just below this range), and the endosteum. For statistical significance the Pearson correlation coefficient was set to $p<0.05$, and no de-noising was performed.

Dried drop analysis of GABA standards was performed by mixing 1 μL of matrix (1:1 CHCA:DHB in 70:30 ACN:$H_2O$+0.1% TFA) with 1 μL of 20 mM GABA in $H_2O$ (to make a final concentration of 10 mM) and spotting on a steel MALDI plate. Laser shots (2000) were summed to generate a spectrum.

Detection of GABA in Extractions of FL and BM Samples by Liquid Chromatography-Mass Spectrometry (LC-MS). Samples were received as homogenized tissue in 5 mL phosphate-buffered saline (PBS). Suspensions were transferred to microcentrifuge tubes and spun at 10 k rpm for 2 minutes to pellet tissue. PBS was removed from microcentrifuge tube and tissue was submerged in 1 mL deionized (DI) $H_2O$, then sonicated for 60 minutes. Extract in DI $H_2O$ was transferred to a new centrifuge tube with 300 μL of $CHCl_3$ and the tube was inverted 5× to separate polar compounds from lipids. $CHCl_3$ was transferred to a new tube, and the process was repeated 2× more. DI $H_2O$ was spun at 10 k rpm for 2 minutes and solvent was transferred to pre-weighed microcentrifuge tube. Extract was dried in vacuo at 30° C. for 2 hours. For quadrupole time-of-flight (Q-ToF) analysis, samples were resuspended in DI $H_2O$ to 10 mg/mL and 10 μL injected for analysis. LC parameters were 2-10% B (A: DI $H_2O$+0.1% TFA, B: ACN+0.1% TFA) over 5 minutes, 98% B for 2 minutes, and 2% B for 2 minutes to re-equilibrate. Tuning Mix ES-TOF (Bruker) was used as an internal calibrant. MS parameters were to detect molecules 100-1000 Daltons in positive mode, and nine precursors were automatically selected for fragmentation per scan. Intensity of GABA was evaluated by selecting an extracted ion chromatogram of m/z 104.0712 (protonated GABA), based on a measured precursor ion from GABA standard (250 μM). Samples were run in duplicate.

Peripheral Blood (PB) Counts. Blood was obtained through retro-orbital bleeding and transferred to EDTA-coated tubes. PB cell numbers were determined using a Vet Abc Hematological analyzer (Scil Animal Care).

Analysis of Different Phenotypically-Defined Hematopoietic Populations. For isolation of BM hematopoietic cells, both femora and tibiae were harvested from postnatal P15 mice after they were euthanized with 3-5% isoflurane. BM cells were collected from bones into PBS containing 2% fetal bovine serum (FBS). For isolation of fetal liver hematopoietic cells, fetal livers were dissected from embryonic day E14.5 embryos. Red blood cells were removed by ACK lysing buffer (Invitrogen) to have mononuclear cells for the following experiments.

Mononuclear cells from BM or fetal liver were incubated with anti-CD16/32 antibody (except CMP, GMP and MEP) to block the Fcγ receptors. The cells were then stained anti-CD3e, anti-CD45R/B220, anti-Gr-1, anti-CD11b, and anti-Ter-119 antibodies (CD11b antibody was excluded in fetal liver cells), and stained with various antibody combinations as shown in Table 1 to analyze Lin$^-$Sca1$^+$cKit$^+$ (LSK) progenitors, HSCs (CD150$^+$CD48$^-$LSK progenitors), MPP1 (CD150$^-$CD48$^-$LSK progenitors), MPP2 (CD150$^+$CD48$^+$LSK progenitors), MPP3/4 (CD150$^-$CD48$^+$LSK progenitors), common lymphoid progenitors (CLP, Lin$^-$Sca1$^{low}$c-kit$^{low}$CD135$^+$CD127$^+$), common myeloid progenitors (CMPs, CD16/32$^-$CD34$^+$ Lin$^-$Sca1$^-$c-kit$^+$ cells), granulocyte-macrophage progenitors (GMPs, CD16/32$^+$CD34$^+$Lin$^-$Sca1$^-$c-kit$^+$ cells), and megakaryocyte-erythrocyte progenitors (MEPs, CD16/32$^-$CD34$^-$Lin$^-$Sca1$^-$c-kit$^+$ cells). 4',6-diamidino-2-phenylindole (DAPI, Sigma, St. Louis, MO) was used to exclude dead cells. For each mouse sample, approximately $1\times10^6$ cells were acquired, and the data were analyzed using BD FACSDiva 6.0 (BD Biosciences, San Jose, CA) and FlowJo (FlowJo, Ashland, OR) software.

The numbers of the different hematopoietic cell populations in each mouse were calculated by multiplying the total numbers of BM cells or FL cells from each mouse or embryo with the frequencies of each population.

Hardy B cell fractions: Mononuclear cells from BM were incubated with anti-CD16/32 antibody to block the Fcγ receptors. The cells were then stained with lineage antibodies anti-CD3e, anti-Gr-1, anti-CD11b, and anti-Ter-119, and stained with anti-B220, anti-CD43, anti-CD24, anti-BP-1, anti-IgM and anti-IgD as shown in Table 1 to analyze different B cell fractions. DAPI was used to exclude dead cells. Fraction A: Lin$^-$CD43$^+$B220$^+$CD24$^-$Bp-1$^-$, Fraction B: Lin$^-$CD43$^+$B220$^+$CD24$^+$Bp-1$^-$, Fraction C: Lin$^-$CD43$^+$B220$^+$CD24$^-$Bp-1$^+$, Fraction D: Lin$^-$CD43$^-$B220$^+$IgM$^-$IgD$^-$, Fraction E: Lin$^-$CD43$^-$B220$^+$IgM$^+$IgD$^-$, Fraction F: Lin$^-$CD43$^-$B220$^+$IgM$^{+/-}$IgD$^+$. All antibody information used in the present study is provided in Table 1.

Secondary HSC Transplantation. Three months after transplantation, $1\times10^6$ bone marrow cells (BMCs) from the recipient mice were used to analyze donor-derived LSK progenitors and HSCs using flow cytometer. BMCs ($1\times10^6$) from the recipient mice were directly injected into lethally irradiated CD45.1 recipients to perform secondary transplantation. In addition, 350 wild-type and Gabbr1$^{-/-}$ HSCs from primary recipients were sorted and mixed with 350 competitive HSCs pooled from CD45.1/2 mice. Mixed cells were then retro-orbitally transplanted into lethally irradiated CD45.1 recipients with $5\times10^5$ CD45.1 spleen cells. The donor cell engraftment ability was determined at two and four months after secondary transplantation using peripheral blood. Four months after secondary transplantation, donor-derived LSK progenitors and HSCs in bone marrow were analyzed using flow cytometer. All antibody information used in the present study is provided in Table 1.

Poly(I:C) Treatment and BrdU Incorporation Assay for Phenotypically-Defined Cells. To measure the responses of wild-type and Gabbr1$^{-/-}$ mice to interferon signaling, P15 mice were peritoneally injected with polyriboinosinic:polyribocytidylic acid (poly(I:C); InvivoGen, San Diego, CA). Forty-eight hours later, mice were euthanized with 3-5% isoflurane and BM cells were utilized for cell cycle and apoptotic analysis in LSK progenitors and HSCs.

To assess proliferating status of hematopoietic cells from wild-type and Gabbr1$^{-/-}$ mice, BrdU (50 mg/kg, BD Biosciences, San Diego, CA) was IP injected into P15 animals. Forty-eight hours later, BrdU incorporation was measured by flow cytometry using the APC BrdU Flow Kit from BD Biosciences (San Diego, CA), following the protocol from the manufacturer, after the cells were stained with antibodies against various cell surface markers. The percentages of BrdU$^+$ cells within the LSK and LSK CD48$^-$ populations were calculated.

Apoptosis Assay for Phenotypically-Defined Cells. Fcγ receptors in BMCs were blocked with anti-CD16/32 antibody at 4° C. for 15 minutes. Cells were then stained with various antibodies against cell surface markers. Annexin V staining was performed with a kit from BD Pharmingen (San Diego, CA) according to the manufacturer's protocol. The ratios of Annexin V positive cells were analyzed within different hematopoietic cell populations using a Fortessa™ flow cytometer.

Caspase 3 Activity Assay. Mononuclear cells from BM were incubated with anti-CD16/32 antibody to block the Fcγ receptors. The cells were then stained with anti-CD3e, anti-CD45R/B220, anti-Gr-1, anti-CD11b, and anti-Ter-119 antibodies, and stained with c-Kit, Sca-1, CD150 and CD48 antibody combinations. Caspase 3 antibody was subsequently added to measure caspase 3 activity using CellEvent™ Caspase-3/7 Green Flow Cytometry Assay Kit (ThermoFisher Scientific Inc.). Caspase 3 activity was expressed as mean fluorescent intensity (MFI).

Cell Cycle Assay for Phenotypically-Defined Cells. BMCs (1×10$^6$) were stained with various antibodies against cell-surface markers and fixed and permeabilized using the Fixation/Permeabilization Solution from BD Biosciences (San Diego, CA). The cells were then stained with anti-Ki67-FITC antibody and 7-AAD (Sigma, St. Louis, MO) for 30 minutes on ice. Cell cycle was analyzed by flow cytometry and Flowjo software.

GAD1 Immunostaining of Sternum BM. Whole mount sternum imaging was performed as previously described (Takaku, et al. (2010) *Blood* 116:e55). Mouse sternums were dissected immediately after euthanasia and connective tissue was removed. Sternum segments were sectioned along the frontal plane and each half was transferred to individual wells in a 96-well plate and incubated with PE-anti mouse B220 (1:200, BioLegend) in 100 μL of ice-cold PBS+2% FBS for 30 minutes. Following staining, specimens were fixed in 4% paraformaldehyde (PFA) for 30 minutes, blocked and permeabilized for 45 minutes in PBS containing 0.25% Triton™ X-100 and 5% donkey serum before incubating with anti-mouse GAD1/GAD-67 (dilution 1:50, Clone F-9, Santa Cruz Biotechnology) overnight at 4° C. After washing, sternum slices were then incubated with donkey anti-Mouse IgG secondary Antibody conjugated to a fluorescent dye sold under the tradename ALEXA FLUOR® 488 (1:2000, Invitrogen) for 1 hour at room temperature followed by DAPI nuclei staining. Confocal images were obtained on a Zeiss LSM710 confocal microscope. Images were processed using ImageJ. All antibody information used in the present study is provided in Table 1.

GAD1 Intracellular Flow Cytometry. BMCs (1×10$^6$) were blocked with CD16/32 antibody and stained with anti-CD93, anti-B220 and anti-CD11b antibodies. Cells were fixed and permeabilized using the Fixation/Permeabilization Solution from BD Biosciences (San Diego, CA). The cells were then stained with anti-GAD1 antibody (Clone F-9, Santa Cruz Biotechnology) for 30 minutes on ice. GAD1 expression was analyzed by flow cytometry and Flowjo software. All antibody information used in the present study is provided in Table 1.

Quantitative RT-PCR. Various populations were directly sorted into RLT Plus buffer (Qiagen). RNA was extracted using the Qiagen RNEASY® minikit or microkit (Qiagen). cDNA was synthesized from RNA with the SUPERSCRIPT® III kit (ThermoFisher Scientific Inc.). Transcripts were amplified with SYBR® Green PCR master mix (Applied Biosystems), and qPCR for Gabbr1 and GAD1 genes was performed on the ABI PRISM® 7900HT system (Applied Biosystems). GAPDH was used as a housekeeping gene. Gabbr1 primers: Forward, 5'-CAAAACAGACAAGTGGATCGGAGG-3' (SEQ ID NO:1); Reverse, 5'-CTGGGAGTTCTGGATATAACGAAC-3' (SEQ ID NO:2). Gad1 primers: Forward, 5'-TCGATTTTTCAACCAGCTCTCTACT-3' (SEQ ID NO:3); Reverse, 5'-GTGCAATTTCATATGTGAACATATT-3' (SEQ ID NO:4).

Ionizing Irradiation. CD45.1 C57BL/6 Female were used for recipients in BM transplantation assay. Six to eight-week-old females were loaded on a rotating platform and exposed to 9.0 Gy of $^{137}$Cesium γ-ray irradiation in an irradiator (J. L. Shepherd, Glendale, CA) at a dose rate of 6.38 Gy/min.

Western Blot Analysis. Brain tissues from wild-type and Gabbr1$^{-/-}$ mice were lysed in lysis buffer (20 mM Tris-HCl, pH 7.4, 150 mM NaCl, 1 mM EDTA, 1 mM EGTA, 10% glycerol, 1.0% NP-40, 0.1 M NaF, 1 mM DTT, 1 mM PMSF, 1 mM NaVO$_4$, 2 μg/mL leupeptin and aprotinin) for 30 minutes on ice. Protein concentration was determined with the Bio-Rad protein assay dye reagent (Bio-Rad). Proteins were separated using SDS-PAGE and transferred to PVDF membranes. Antibodies used for western blot included a GABBR1 mouse monoclonal antibody specific for an epitope mapping between amino acids 929-958 at the C-terminus of GABA$_B$ R1 of rat origin (clone D-2; Santa Cruz Biotechnology, Santa Cruz, CA); GAPDH (Sigma, St. Louis, MO); and secondary anti-rabbit-HRP, anti-goat-HRP or anti-mouse-HRP (Pierce). Blots were visualized with SuperSignal™ West Femto chemiluminescent substrate (ThermoFisher Scientific, Waltham, MA).

In vitro B Cell Differentiation Assay. LSK progenitors (4,000) from wild-type and Gabbr1$^{-/-}$ mice were directly sorted onto pre-prepared OP9 stromal cells with 1 mL complete DMEM medium containing 10% FBS, 1 ng/mL IL-7, and 5 ng/mL Flt-3L. Three and six days later, 1 mL complete DMEM medium was added. One week after initial culture, all cells including OP9 cells were mechanically detached and filtered with a 7-μm cell strainer. Cells were passaged onto fresh OP9 stromal cells with complete medium. Medium was changed every three days. At 14 days after initial culture, all cells were detached and stained with CD45.2, CD19, B220 and CD11b antibodies. The numbers of the different hematopoietic cell populations in each well were calculated by multiplying the total cell numbers from each well with the frequencies of each population. To assess the effects of Gabbr1 on myeloid cell differentiation from LSK cells, the DMEM medium containing 10% FBS, 1 ng/ml IL-7, 5 ng/ml Flt-3L, 5 ng/ml IL-6, 6 ng/ml IL-3 was used. Fourteen days after sorted LSK cells were cultured on OP9 cells, numbers of CD11b$^+$ and Gr-1$^+$ cells were measured via flow cytometry. All antibody information used in this analysis is provided in Table 1.

Mouse Hematopoietic Progenitor Cell Colony Assays. Assays were performed as previously described (Broxmeyer, et al. (2012) *Nat. Med.* 18:1786-1796; Mantel, et al. (2015) *Cell* 161:1553-1565; Capitano, et al. (2018) *Blood* 132:1027-1038; Capitano, et al. (2019) *Clin. Invest.* 129: 2555-2570). Bone marrow cells were harvested from two tibias by flushing with DPBS (HYCLONE™) Splenocytes were isolated from spleens by homogenizing individual spleens through a 70-pM mesh (Fisher) using DPBS. Colony forming units (CFU)-granulocyte macrophage, burst forming units (BFU)-erythroid (E), granulocyte, erythrocyte, macrophage, and megakaryocyte (GEMM) colonies were scored after 7 days in culture by plating whole bone marrow at $5\times10^4$ cells/mL and splenocytes at $2\times10^5$ cells/mL in 1% methylcellulose/Iscoves Modified Dulbeccos Medium (IMDM) with 30% FBS (Corning), 1 U/mL erythropoietin (Amgen), 5% (v/v) pokeweed mitogen spleen cell conditioned medium (PWMSCM), 50 ng/mL recombinant mouse stem cell factor (rmSCF, R&D Systems), and 0.1 mM Hemin (Sigma). Cultures were incubated at 37° C. with 5% $CO_2/O_2$. Absolute numbers of progenitors were calculated based on nucleated cell counts. Colonies were identified by the type of cells they contained: BFU-E contained only erythroid cells, as defined by their characteristic red color, with hemin enhancing this color; CFU-GEMM contained GM cells, erythroid cells, and usually have megakaryocytes. The tritiated thymidine cell kill procedure was performed according to established methods (Broxmeyer, et al. (2012) *Nat. Med.* 18:1786-1796; Mantel, et al. (2015) *Cell* 161: 1553-1565; Capitano, et al. (2018) *Blood* 132:1027-1038; Capitano, et al. (2019) *Clin. Invest.* 129:2555-2570; Gotoh, et al. (1996) *Blood* 88:138-145). Briefly, to calculate percent of progenitors in S-Phase of the cell cycle (an estimate of cell cycling) cells were pulsed with or without high specific activity tritiated thymidine (1 mCi/mL, Perkin Elmer) for 30 minutes at 37° C. Cells were then washed and plated, and the differences in number of each type of colony between cells pulsed with control media and high specific activity tritiated thymidine was used to calculate the percent of each type of colony in S-phase of the cell cycle.

Human Umbilical Cord Blood (UCB) Colony Forming Assays. Colony forming assays were carried out with either CD34$^+$ UCB progenitors treated as above prior to xenotransplant (i.e., input cells), or from xenotransplant recipient BM after 16 weeks (i.e., output cells). Input cells were plated at a density of $1\times10^3$ cells/dish. Output cells were plated at a density of $2\times10^5$ cells/dish. Cells were mixed with METHOCULT® M3434 culture medium (STEMCELL Technologies) and plated into each of three 35-mm gridded dishes. Dishes were incubated at 37° C. for 12 days and colonies were enumerated under a bright light microscope. A clonogenic colony contained at least 50 cells or greater.

CD34$^+$ UCB Cell Xenotransplants into NSG Mice. All NSG studies were carried out in accordance with, and approval of the Institutional Animal Care and Use Committee of Indiana University School of Medicine and the *Guide for the Care and Use of Laboratory animals*. Female NOD.Cg-Prkdc$^{scid}$ Il2rg$^{tm1Wjl}$/Szj (NSG) mice were obtained from the In Vivo Therapeutics Core of the Indiana University Simon Cancer Center. Animals were maintained under pathogen-free conditions and maintained on Irradiated Global 2018 (Uniprim 4,100 ppm; Harlan Laboratories) food pellets with ad libitum access to autoclaved, acidified tap water under a 12-hour light-dark cycle at 22° C. to 24° C. Mice were irradiated 4 hours prior to transplant (3.0 Gy of $^{137}$Cesium γ-ray irradiation in an irradiator (J. L. Shepherd, Glendale, CA) at a dose rate of 88 cGy/min). CD34$^+$ UCB cells were thawed in 1% human serum albumin in STEMSPAN® media (STEMCELL Technologies) with human SCF 100 ng/ml and allowed to sit for 2 hours. Cells were then counted and plated at $0.5\times10^6$ cells/mL in STEMSPAN® media with 1% HSA. Cells were plated and treated with the following for 2 hours at 37° C.: 1, 10, or 50 μM (RS)-Baclofen (Tocris); 1, 10, or 50 μM 2-hydroxysaclofen (Tocris); vehicle control (DMSO). Cells were harvested and immediately washed with PBS by centrifugation at 300×g for 10 minutes. Mice were transplanted with 20,000 cells each in 200 μL PBS (n=7 mice per group). PB and BM were harvested at 16 weeks post-transplant.

Analysis and Multi-Parametric Flow Cytometry Immunostaining of Xenotransplant Mice. For peripheral blood counts, blood was obtained through retro-orbital bleeding and transferred to EDTA-coated tubes. Peripheral blood cell numbers were determined using a Vet Abc Hematological analyzer (Scil Animal Care). For PB, BM, and spleen analysis of the target populations in xenotransplant mice, the cells were collected using a red blood cell lysis assay (eBioscience). The following primary conjugated monoclonal antibodies were used: anti-human CD34 PE (BD Pharmingen), anti-human AC133 APC (Miltenyi Biotec), anti-human CD19 PECy7 (BD Pharmingen), anti-human CD33 PerCP-Cy5.5 (BD Pharmingen), anti-human CD38 FITC (BD Pharmingen), anti-human CD45 APC-fluorescent dye sold under the tradename ALEXA FLUOR® (AF) 750 (Invitrogen), and the fixable amine reactive viability dye, LiveDead (Violet, Invitrogen).

The lysed PB, BM, and spleen cells were incubated with both human and murine Fc blocking reagent (Miltenyi Biotec) for 10 minutes on ice. Briefly, cells were incubated with the titered antibodies listed above for 30 minutes at 4° C., washed twice in PBS with 2% fetal bovine serum, fixed in 1% PFA (Tousimis), and analyzed within 24 hours on a BD Fortessa™ flow cytometer (BD, Franklin Lakes, NJ, USA) equipped with a 405 nm violet laser, 488 nm blue laser, 640 nm red laser, and 561 nm yellow-green laser. Approximately 100,000 events per sample were acquired uncompensated and exported as FCS 3.1 files, and analyzed utilizing FlowJo software, version 9.9.6 (Tree Star, Inc). "Fluorescent minus one" (FMO) gating controls were also used to ensure proper gating of positive events (Estes, et al. (2010) *Curr. Prot. Cytometry* 9:9.33.331-11; Estes, et al. (2010) *Cytometry Part A* 77:831-839).

Statistical Analysis. The data were presented as mean±SD. Analysis of variance (ANOVA) was used for data analysis. For experiments, single experimental and control groups were used, the differences were analyzed by an unpaired Student's t test. Differences among the groups were analyzed by Student-Newman-Keuls multiple comparisons test after two-way ANOVA. $p<0.05$ was considered a significant difference. GraphPad Prism™ from GraphPad Software were used for all analyses.

Analysis of Published Single Cell RNA-Seq Gene Expression Profiles of Hematopoietic Stem and Progenitor Cells (HSPCs). The count data for the previously published single cell gene expression data set (Nestorowa, et al. (2016) *Blood* 128:e20-e31) was directly downloaded. Data were processed by the Scatter library from the R Bioconductor resource. Gabbr1 expression was assessed for contribution to different clusters. To identify genes with expression correlated to Gabbr1, a linear correlation was used and the correlated genes were ranked by their correlation co-efficient. Next, gene set enrichment analysis (GSEA) software was applied using the biological process sets from the Gene Ontology (Subramanian, et al. (2005) *Proc. Natl. Acad. Sci. USA* 102:15545-15550) on a ranked list of genes using the correlation scores. In this way, genes with high positive correlation were co-expressed and co-regulated with Gabbr1, while negatively correlated genes were not expressed and showed opposite expression regulation (repressed when Gabbr1 is expressed). Enriched gene sets were assessed by the FEWER adjusted p-value for significance and those with a value of <0.05 were accepted as significant.

Bulk RNA-Seq Sample Preparation. LSK cells (~12,000) from P15 wild-type (n=4) or Gabbr1 null (n=4) BM were sorted (MoFlo Astrios) and collected in an acid-guanidinium-phenol based reagent sold under the tradename TRIZOL® LS (Invitrogen). Volumes were adjusted to a final ratio of 3:1 for TRIZOL® LS and nuclease-free water. Samples were stored at −80° C. until total RNA was isolated. Then samples were thawed, equilibrated to room temperature, and divided into 800 µL aliquots. Five pg of Sigma "GenElute™" linear polyacrylamide (LPA), diluted in nuclease-free water, was added to each aliquot and vortexed for 30 seconds. Chloroform extraction and three ethanol washes were performed as per the TRIZOL® product insert (Invitrogen protocol). The pellet was resuspended in 6 pL RNAse-free water.

Bulk RNA-Seq Library Preparation and Sequencing. RNA samples were quantified and purity and integrity were checked using NANODROP® One Spectrophotometer (Thermo Scientific) and Agilent 4200 TAPESTATION®. NGS library preparation was completed using NuGen's OVATION® SoLo RNA-Seq Systems, per the User Guide M01406 v4, including a targeted depletion with SoLo ANY-DEPLETE® Mouse Probe Mix. RNA input into library preparation was between 3.6-5 ng. The number of cycles for the first library PCR amplification were optimized using qPCR, as outlined in the SoLo User Guide, with the Prime Pro 48 Real-Time PCR system (Techne).

Completed libraries were quantified using Qubit fluorometer (Invitrogen) and size was determined using TAPESTATION®. Libraries were pooled based on Qubit dsDNA concentration and run on MISEQ® for index balancing. The second pool, with corrected library inputs based on the % Reads Identified (PF) results from the MISEQ® run, was purified with 1:1 AGENCOURT® AMPURE® XP beads. The final, purified pool was quantified using Qubit and pool size was determined using TAPESTATION®. Sequencing was run on a NovaSeq6000 SP flow cell, 2×50 bp, two lanes, at the University of Illinois Roy J. Carver Biotechnology Center High-Throughput Sequencing and Genotyping Unit.

Bulk RNA-Seq Data Analysis. After library preparation and sequencing, raw reads were aligned to reference genome mm10 using STAR (Dobin, et al. (2013) *Bioinformatics* 29:15-21). ENSEMBL genes were quantified using FeatureCounts (Liao, et al. (2014) *Bioinformatics* 30:923-930). Differential expression statistics were computed using edgeR (Robinson, et al. (2010) *Bioinformatics* 26:139-140; McCarthy, et al. (2012) *Nucl. Acids Res.* 40:4288-4297) on raw expression counts with the exactTest function. Principal component analysis (PCA) identified outlier samples that were removed from further analysis. The final analysis included n=2 wild-type samples and n=3 Gabbr1 null samples. P-values were adjusted for multiple testing using the false discovery rate (FDR) correction of Benjamini and Hochberg ((1995) *J. Royal Stat. Soc. Series B* 57:289-300). Data were analyzed through the use of IPA to find "Ingenuity Canonical Pathways" that were associated with genes expressed at higher or lower levels in Gabbr1 null relative to wild-type (QIAGEN). For pathway enrichments, up and down-regulated genes were determined based on a FDR cutoff of 0.1 and compared to single-cell RNA-seq gene lists from Miyai et al. ((2018) *Genes Dev.* 32:112-126) using Fisher's Exact Test.

Example 2: Hematopoietic Stem and Progenitor Cells Express Gabbr1

Gabbr1 expression was investigated in mouse HSPCs, and presence of its neurotransmitter, GABA, in the BM. Published HSPC microarray and single-cell RNA-sequencing data were re-analyzed for Gabbr1 expression. A recent study (Zhu, et al. (2019) *Proc. Natl. Acad. Sci. USA* 116 (37):18416-18422) did not score Gabbr1 as expressed in HSPCs because of low levels in bulk microarray data from Gene Expression Commons (GEXC)(Seita, et al. (2012) *PLoS ONE* 7(7):e40321). Despite low expression levels of Gabbr1 in HSPCs, it has now been found that relative levels are higher in HSCs compared to more differentiated progenitors, with the exception of common lymphoid progenitors (CLPs) that have the highest expression level of Gabbr1. Single cell RNA sequencing data were analyzed from three independent studies that detected Gabbr1 in a subset of HSPCs (Nestorowa, et al. (2016) *Blood* 128(8):e20-e31; Olsson, et al. (2016) *Nature* 537:698-702; Weinreb, et al. (2018) *Bioinformatics* 34(7):1246-1248). To confirm published results, flow cytometry was used to test for Gabbr1 receptor surface expression in BM HSPCs. A distinct population of Lin$^-$Sca1$^+$cKit$^+$ (LSK) progenitors (~12%), and HSCs (LSK/CD48$^-$/CD150$^+$; ~15%), had detectable Gabbr1 surface expression, indicating that Gabbr1 is expressed in a subset of BM resident HSPCs, including HSCs.

Example 3: GABA is Present in the Adult Bone Marrow Endosteal Region

The cell type that produces GABA in BM was identified based on expression of glutamate decarboxylase enzymes GAD1 or GAD2 that convert glutamic acid to GABA (Erlander, et al. (1991) *Neuron* 7(1):91-100). It was suggested that non-neural cells in the BM were candidates for GABA production, however the specific cell type was not determined (Zhu, et al. (2019) *Proc. Natl. Acad. Sci. USA* 116(37):18416-18422). Single-cell RNA-sequencing data of BM stromal cells did not reveal a cell type clearly expressing Gad1 or Gad2 (Baryawno, et al. (2019) *Cell* 177 (7):1915-1932 e1916). However, Haemopedia RNA-seq and microarray data of mouse hematopoietic populations found Gad1 (but not Gad2) was strongly enriched in B cells (Choi, et al. (2019) *Nucl. Acids Res.* 47(D1):D780-D785; de Graaf, et al. (2016) *Stem Cell Rep.* 7(3):571-582). Quantitative PCR analysis of sorted B cells confirmed expression of Gad1 transcript. Intracellular flow cytometry analysis of B220$^+$ CD93$^-$ B cells found 77.7% were positive for Gad1, whereas CD11b$^+$ myeloid cells were negative. These results were confirmed by immunofluorescence analysis of mouse BM sternum that showed B220$^+$ B cells, but not CD11b$^+$ myeloid cells, were positive for Gad1. Intracellular flow cytometry and immunofluorescence analysis were repeated using BM from Rag1$^{-/-}$ mutants that lack B cells (Mombaerts, et al. (1992) *Cell* 68(5):869-877). Gad1 expression was largely absent in BM of these B cell-deficient mutants.

Together, this establishes Gabbr1 receptor expression by a subset of HSPCs, including HSCs, and that B cells express Gad1 enzyme.

It was subsequently determined whether endogenous GABA molecules are present in the BM. To achieve spatial mapping of GABA across different regions of the BM niche, IMS analysis was performed (Gessel, et al. (2014) *J. Proteomics* 107:71-82). IMS is label-free and allows for direct detection and relative quantification of endogenous metabolites. Femur sections from wild-type adult mice were spotted with commercial GABA standard as an internal control. IMS was performed at spatial resolution of 20 µm, and data were normalized to root mean square. GABA ions were detected in BM sections (n=4), and both the protonated molecule ($C_4H_{10}NO_2^+$, $[M+H]^+$, m/z 104), as well as the dehydrated ion ($C_4H_8NO^+$, $[M-H_2O+H]$, m/z 86), were detected with high intensity in the standard and femur. Upon visual analysis of the IMS data, the m/z 86 and m/z 104 ions had the same spatial distribution in the samples. In the standard, the limit of detection was between 100 µM and 1 mM GABA. High-resolution detail from BM diaphysis shows m/z 86 is highly localized to the outer endosteal region.

To confirm detection of a molecule with a different spatial distribution in the BM, IMS was used to detect heme, an indicator of erythrocyte localization. Heme was at high levels within the central sinus that carries large blood volumes. Both unbound ($[M+H]^+$, m/z 567) and iron-bound ($[M+H]^+$, m/z 616) heme was detected in the central region of the BM, and was distinct from endosteal localization of GABA.

Following the finding that B cells express GABA-producing enzyme Gad1, and are potential sources of GABA, IMS was used to evaluate relative contributions of B cells to GABA levels in the BM. While IMS is not completely quantitative, the limit of detection, determined by ionization efficiency of the standard, provides general measure of GABA amounts produced in BM. GABA levels were compared in $Rag1^{-/-}$ and wild-type femur sections. GABA levels were significantly lower in $Rag1^{-/-}$ B cell-deficient bones. Representative IMS data shows GABA levels reduced in the endosteal region of $Rag1^{-/-}$ femur.

Example 4: Gabbr1 Null Mutants have Reduced Numbers of Hematopoietic Progenitors and B Lymphocytes Reports established a neurological phenotype in Gabbr1 loss-of-function mouse mutants on various genetic backgrounds (Schuler, et al. (2001) *Neuron* 31(1):47-58; Prosser, et al. (2001) *Mol. Cell. Neurosci.* 17(6):1059-1070; Quéva, et al. (2003) *Br. J. Pharmacol.* 140(2):315-322). To conduct consistent hematopoietic analysis, a Gabbr1 null ($Gabbr1^{-/-}$) mutant was generated on a C57BL/6 background using CRISPR/Cas9 gene editing. Guide RNAs designed to target Gabbr1 exon 5, which is shared by all isoforms, generated a nonsense mutation due to a one base pair adenine insertion (+1 bp [A]). Mutants were undersized compared to littermates and had slightly reduced body weight. Loss of Gabbr1 protein was confirmed by western blot of brain tissue. The Gabbr1 null mutants phenocopied those previously generated on other mutant backgrounds, as confirmed by spontaneous seizures and failure to survive beyond P20 because of neurological defects (Schuler, et al. (2001) *Neuron* 31(1):47-58; Prosser, et al. (2001) *Mol. Cell. Neurosci.* 17(6):1059-1070; Quéva, et al. (2003) *Br. J. Pharmacol.* 140(2):315-322).

Given specific expression of Gabbr1 in a subset of HSPCs, BM and peripheral blood (PB), $Gabbr1^{-/-}$ mutants were analyzed for hematopoietic phenotype. Due to poor survival, analysis was consistently performed at P15.

Characterization of LSK progenitors showed moderate but consistent (n=9) defects in absolute numbers of BM cells of $Gabbr1^{-/-}$ mice. No significant differences were observed in the long-term hematopoietic stem cell (LT-HSC) population and in total bone marrow cellularity. Other populations, such as multi-potent progenitor populations MPP1-3, were also analyzed and showed pronounced decreases in numbers. Downstream of LSKs, significant decreases were only observed in percentages and absolute numbers of CLPs. BM B-cell developmental stages were analyzed by Hardy Fraction markers (Hardy, et al. (1991) *J. Exp. Med.* 173(5):1213-1225; Petkau, et al. (2019) *Biochem. J.* 476(5):769-778) and dramatic decreases in abundance of fractions B-through-E were detected. Consistent with this, PB showed defects in white blood cells (WBC) and lymphocytes, but not in neutrophils. Flow cytometry indicated that PB $B220^+$ B-cells were significantly reduced, with no differences in $CD4^+$ T-cells, $CD11b^+$ and $Gr1^+$ myeloid cells, or red blood cells and hemoglobin content. Platelet counts were moderately decreased. This indicates that loss of Gabbr1 affects abundance of LSK progenitors, without significant effects on phenotyped LT-HSCs, and that developmental defects in BM maturation of B-cell lymphocytes are the primary defects in PB.

Since the constitutive whole-body $Gabbr1^{-/-}$ mutants have an early hematopoietic phenotype at P15, it was determined whether there was any hematopoietic development disruption in FL. Timed matings of $Gabbr1^{+/-}$ parents produced viable E14.5 embryos with no apparent gross morphological phenotype. FL analysis indicated no significant difference in the number of phenotyped LSK progenitors and LT-HSCs between $Gabbr1^{-/-}$ and $Gabbr1^{+/+}$ littermates. To determine if the Gabbr1-GABA axis was present in the FL, mass spectrometry was performed to detect GABA ion in whole BM of P15 mice and the FL of E14.5 embryos. GABA was not detected in the E14.5 FL. This reveals a specific BM niche requirement for Gabbr1 not applying to development of HSPCs in FL.

Example 5: Hematopoietic Reconstitution Potential is Impaired by Loss of Gabbr1

The results herein indicate that hematopoietic defects in P15 $Gabbr1^{-/-}$ mutants are specific to phenotypic LSK progenitors, but not LT-HSCs. As mutants are constitutive knockouts, their hematopoietic phenotypes could be due to Gabbr1-dependent BM niche defects. To confirm that the LSK progenitor defect is cell autonomous, and to test functionality of hematopoietic cells that lack Gabbr1, since phenotype does not always recapitulate function of HSPCs (Chen, et al. (2019) *Leukemia* 33(12):2962-2966), direct transplantation of $1\times10^6$ whole BM cells from $Gabbr1^{+/+}$ or $Gabbr1^{-/-}$ P15 littermates were performed into lethally irradiated $CD45.1^+$ wild-type recipient mice in a non-competitive assay. Reconstitution was monitored every 4 weeks post-transplant for 3 months. Within the first 4 weeks, a significant defect in total PB reconstitution was observed in the percentage of $CD45.2^+$ $Gabbr1^{-/-}$ donor cells. However, by 2 months post-transplant, $CD45.2^+$ $Gabbr1^{-/-}$ donor cells overcame this initial deficit and fully reconstituted irradiated recipients. This indicates the phenotype one-month post-transplant may result from defects in short-term HSCs or progenitors, and recovery of reconstitution could be due to LT-HSCs. Thus, the transplant experiment was repeated, but instead of whole BM, 350 sorted CD45.2$^+$ LT-HSCs (LSK/CD48$^-$/CD150$^+$) from BM of P15 Gabbr1$^{+/+}$ or Gabbr1$^{-/-}$ donors were used and injected along with 5×10$^5$ CD45.1/2 splenic support cells. Again, CD45.1$^+$ recipients transplanted with CD45.2$^+$ Gabbr1$^{-/-}$ donor cells showed an initial deficit in PB reconstitution but recovered to wild-type levels by 2 and 3 months after transplant. While this indicated a cell-autonomous role for Gabbr1 in hematopoietic stem and/or progenitor cells, the dynamics of reconstitution by Gabbr1 null cells was still not clear.

It was hypothesized that loss of Gabbr1 in a competitive transplant would permanently affect hematopoietic recovery since it would test the fitness and ability of Gabbr1-null LT-HSCs to compete for the same niche with wild-type LT-HSCs. Accordingly, 350 sorted LT-HSCs, harvested from BM of Gabbr1$^{+/+}$ or Gabbr1$^{-/-}$ littermates, were transplanted in competition with 350 BM LT-HSCs from a CD45.1/.2 donor, along with CD45.1 splenic support cells. In this competitive setting, defects in Gabbr1$^{-/-}$ PB reconstitution persisted for 3 months, confirming lack of Gabbr1$^{-/-}$ cell fitness. Interestingly, lineage contributions of transplanted Gabbr1$^{-/-}$ HSCs to PB was reduced in lymphoid, but not myeloid compartments. Numbers of Gabbr1$^{-/-}$ BM CD45.2$^+$ LSK progenitors and LT-HSCs were significantly reduced at 3 months, as were several progenitor populations.

To determine the extent of the competitive reconstitution defect, secondary transplants were performed with either 1×10$^6$ whole BM cells harvested from primary competitive recipients, or by sorting 350 CD45.2$^+$ LT-HSCs derived from primary recipient BM, and initiating a secondary competition with 350 HSCs from a CD45.1/.2 donor. In whole BM secondary competitive transplant, the ratio of wild-type to Gabbr1$^{-/-}$ reconstitution was maintained, demonstrating that these defects were in a self-renewing HSC population; terminal analysis revealed dramatic decreases in percentage of LSK progenitors and LT-HSCs. Secondary competitive transplant with 350 sorted Gabbr1$^{-/-}$ LT-HSCs also showed significant defects in reconstitution. At the terminal 4-month timepoint, BM analysis of the recipients indicated decreased overall Gabbr1$^{-/-}$ cellularity and significant defects in LSK progenitors and LT-HSC frequency. In both cases, reconstitution defects persisted up to 4 months after secondary transplants. These results indicate that there is a cell autonomous role for GABBR1 in hematopoietic reconstitution, and in HSPC competitive fitness.

Example 6: Proliferative Capacity of HSPC Pool in Gabbr1$^{-/-}$ Mutants is Reduced To understand Gabbr1 signaling in HSPCs, cell cycle and apoptotic assays were performed in phenotypic populations of BM LSK progenitors of wild-type and Gabbr1$^{-/-}$ P15 littermates. Ki-67 and 7-AAD counterstaining determined LSK progenitor cell cycle progression. Flow cytometry for quantification of LSK cell cycle indicated significant defects in Gabbr1$^{-/-}$ LSKs during cell growth and entry into G1 phase. However, pro-apoptotic analysis by AnnexinV staining or Caspase 3 activity of LSK progenitors and HSCs in the BM showed no difference between Gabbr1$^{-/+}$ and Gabbr1$^{-/-}$ P15 littermates.

Phenotypic analysis of HSPCs confirms their presence, but it does not allow assessment of functional characteristics of these cells (e.g., their proliferative and differentiation capacity). For functional progenitor capacities, colony assays are used. This allows one to determine proliferative capacity, and percent of specific progenitor cell types (CFU-GM, BFU-E, and CFU-GEMM) in S-phase of the cell cycle (cycling rate), by using a well-established high specific activity tritiated thymidine cell kill procedure (Capitano, et al. (2018) *Blood* 132(10):1027-1038; Capitano, et al. (2019) *J. Clin. Invest.* 129(6):2555-2570; Mantel, et al. (2015) *Cell* 161(7):1553-1565; Broxymeyer, et al. (2012) *Nat. Med.* 18(12):1786-1796; Gotoh, et al. (1996) *Blood* 88(1):138-145). Functional BM progenitors CFU-GM, BFU-E, and CFU-GEMM of Gabbr1 and Gabbr1$^{-/-}$ littermate mice (P13-15) were evaluated. Absolute numbers of BM CFU-GM in Gabbr1$^{-/-}$ mice were significantly decreased compared to Gabbr1 BM. Almost all Gabbr1$^{-/-}$ progenitors were in a slow or non-cycling state. No difference in size or appearance of colonies were noted.

To understand proliferation defects in Gabbr1$^{-/-}$ mutant HSPCs, a bioinformatics approach was used to find common characteristics among subsets of HSPCs expressing Gabbr1. Gene set enrichment analysis (GSEA; Subramanian, et al. (2005) *Proc. Natl. Acad. Sci. USA* 102(43):15545-15550) was performed based on ranked correlation of co-expressed genes from previously published single HSPC RNA-seq data (Nestorowa, et al. (2016) *Blood* 128(8):e20-e31). Four of the top ten gene ontology (GO) annotations that correlated positively with Gabbr1 expression were associated with type I or II interferon signaling (Table 2).

TABLE 2

| GO TERM | Adjusted FWER P value |
|---|---|
| GO_IMMUNE_RESPONSE | 0 |
| GO_RESPONSE_TO_INTERFERON_GAMMA | 0 |
| GO_ADAPTIVE_IMMUNE_RESPONSE | 0 |
| GO_CELLULAR_RESPONSE_TO_INTERFERON_GAMMA | 0 |
| GO_REGULATION_OF_CYCLIC_NUCLEOTIDE_METABOLIC_PROCESS | 0 |
| GO_REGULATION_OF_RHO_PROTEIN_SIGNAL_TRANSDUCTION | 0 |
| GO_POSITIVE_REGULATION_OF_RESPONSE_TO_WOUNDING | 0.001 |
| GO_NEGATIVE_REGULATION_OF_LYMPHOCYTE_DIFFERENTIATION | 0.001 |
| GO_INTERFERON_GAMMA_MEDIATED_SIGNALING_PATHWAY | 0.001 |
| GO_RESPONSE_TO_TYPE_I_INTERFERON | 0.001 |

To test in vivo the prediction that Gabbr1 is involved in type I interferon response, a known regulator HSPC proliferation (Pietras, et al. (2014) *J. Exp. Med.* 211(2):245-262), wild-type and Gabbr1$^{-/-}$ P15 littermates were treated with an intraperitoneal (IP) injection of poly(I:C). BM analysis of wild-type and Gabbr1$^{-/-}$ littermates 48 hours after poly(I:C) injection indicated significant decreases in numbers of Gabbr1$^{-/-}$ progenitors; Ki-67 and 7-AAD cell cycle analysis, further confirmed a G1-entry defect in Gabbr1$^{-/-}$ progenitors. Poly(I:C) treatment had no effect on the pro-apoptotic status of Gabbr1$^{-/-}$ LSK progenitors. To determine if G1-entry defects in LSK progenitors continued to affect Gabbr1$^{-/-}$ mutants during S-phase, BrdU IP was injected into P15 wild-type and Gabbr1$^{-/-}$ littermates and BrdU incorporation was analyzed by flow cytometry in LSK progenitors and long-term HSCs 48 hours later. For both populations, significant decreases in BrdU incorporation were observed, confirming defects in proliferative capacity of phenotypically-defined Gabbr1$^{-/-}$ hematopoietic progenitors and stem cells.

Example 7: Differentiation of Gabbr1$^{-/-}$ Mutant Progenitors In Vitro Reveals Proliferation Defects in B-Cell Lineages To assess whether loss of Gabbr1 affects overall proliferation of progenitors, or whether it has specific consequences in lineage commitment, OP9 stromal cells were employed for lymphoid and myeloid differentiation of sorted BM progenitors. Using previously described OP9 conditions (Holmes, et al. (2009) *Cold Spring Harb Protoc.* 2009(2): pdb.prot5156), 4,000 LSK progenitors from P15 Gabbr1$^{-/-}$ or Gabbr1$^{+/+}$ littermates were differentiated into myeloid or B-cell lymphoid lineages. After 2 weeks, overall cellular content and phenotypic analysis of differentiated lineages were conducted. Results indicated decreased overall numbers of CD45$^+$ cells produced by Gabbr1$^{-/-}$ LSK progenitors, in accordance with in vivo analysis of proliferation defects in the mutants. Furthermore, a significant defect in B-cell lineage development was indicated by reduced CD19$^+$ and B220$^+$ cells originating from Gabbr1$^{-/-}$ mutants. No defect was detected in the myeloid compartment as indicated by presence of CD11b$^+$ cells. This was confirmed by repeating differentiation assays by supplementing pro-myeloid cytokines IL-3 and IL-6 to the OP9 differentiation media. There was no significant difference in expanded myeloid compartments between wild-type and Gabbr1$^{-/-}$ mutant progenitors. Overall, this supports the in vivo analysis of Gabbr1$^{-/-}$ mutants by confirming defects in progenitor proliferation, and in B-cell differentiation.

Example 8: B Cell Program Genes are Dysregulated in Gabbr1$^{-/-}$ Mutant HSPCs

To better understand molecular phenotypes of Gabbr1$^{-/-}$ mutant HSPCs, ~12,000 LSKs from Gabbr1$^{+/+}$ or Gabbr1$^{-/-}$ P15 BM were sorted and pooled for bulk RNA-seq analysis. After initial comparison of differentially expressed genes between wild-type and mutant LSKs, and Ingenuity Pathway Analysis (IPA; Kramer, et al. (2014) *Bioinformatics* 30(4):523-530), significant increases in expression of genes associated with B cell development were observed in mutant LSKs (Ratio=0.33; −log(B-H p-value)=8.69). To further investigate these changes, a "blueprint" for B cell development was used to generate custom gene sets (Miyai, et al. (2018) *Genes Dev.* 32(2):112-126). These sets were associated with progressive stages of in vitro multipotent progenitor differentiation into B lymphocytes, or sorted BM populations of phenotypically-defined lymphoid-primed multipotent progenitors (LMPP), common lymphoid progenitor (CLP), and Pro-B cells. Gene signatures from the first and earliest stages of B lineage differentiation, or sorted LMPPs, were significantly enriched in wild-type HSPCs compared to Gabbr1$^{-/-}$ HSPCs; alternatively, this could be interpreted as down-regulation of early progenitor-associated genes in mutant HSPCs. The second stage of B cell differentiation or "transition" (Miyai, et al. (2018) *Genes Dev.* 32(2):112-126) is similar to a CLP. This gene signature is mixed, with some representative genes in wild-type, and some in Gabbr1$^{-/-}$ mutant HSPCs. Later stage B cell commitment and pro-B cell gene signatures (Miyai, et al. (2018) *Genes Dev.* 32(2):112-126) are very highly enriched in Gabbr1$^{-/-}$ mutant HSPCs. This demonstrates significant shifts in expression profiles of LSK HSPCs from early progenitor-like signature to that of committed pro-B cells, indicating that Gabbr1 plays a role in differentiation of HSPCs to B lineage cells.

Figure 2:
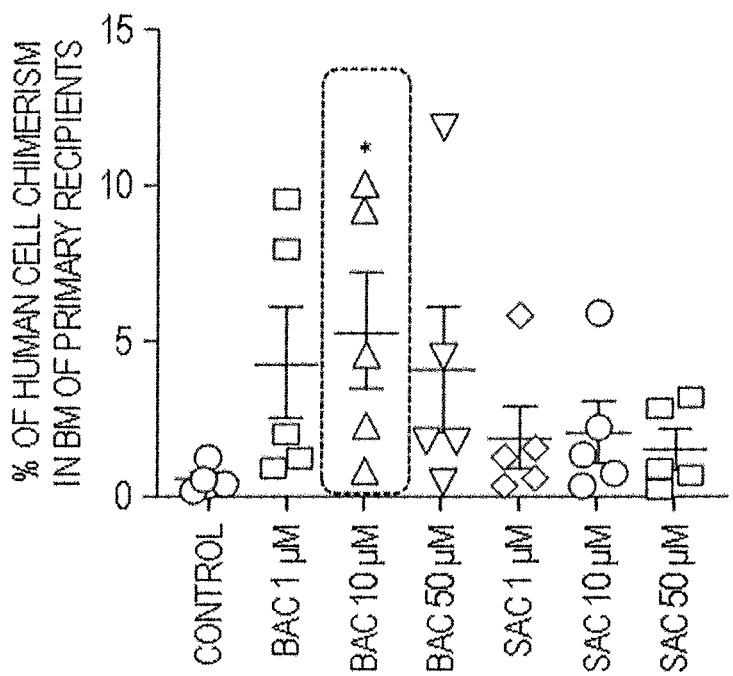
FIG. 2 show percent engraftment of human $CD34^+$ hematopoietic stem and progenitor cells in mouse recipients 16 weeks post-transplant. Prior to transplant, cells were treated ex vivo for 2 hours at 37° C. in media with GABA B Receptor 1 (GABBR1) agonist (Baclofen; "Bac") or antagonist (hydroxy-Saclofen; "Sac").
Figure 3:
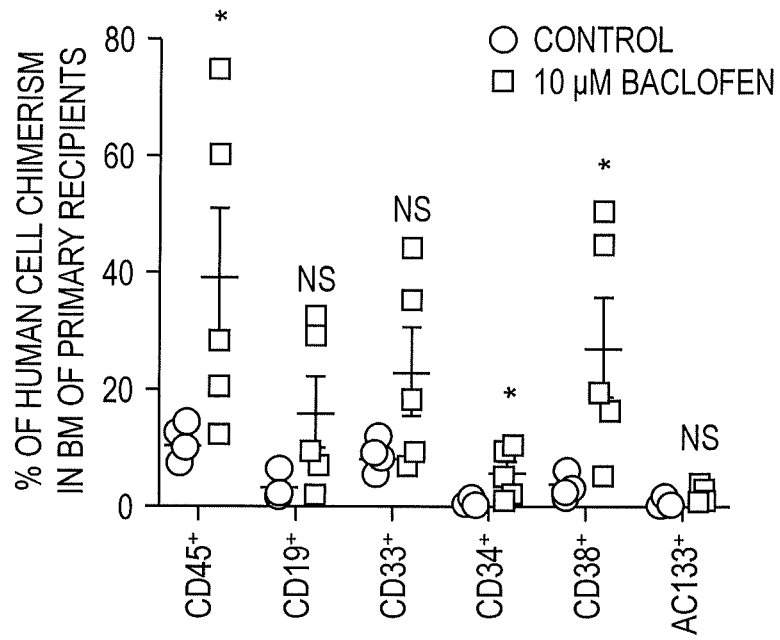
FIG. 3 shows a comparison of % engraftment of various hematopoietic populations in bone marrow (BM) using a 10 µM dose of Baclofen. NS, not significant.
Figure 4:
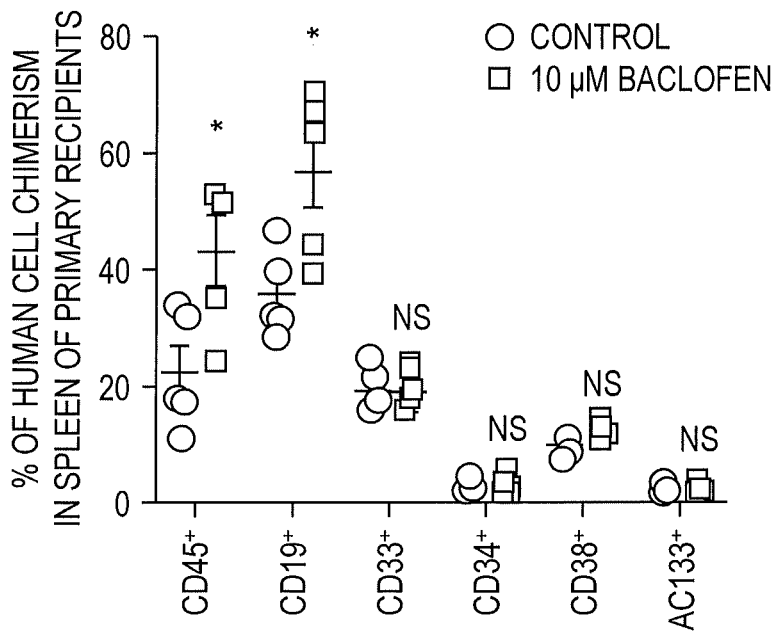
FIG. 4 shows a comparison of % engraftment of various hematopoietic populations in spleen using a 10 µM dose of Baclofen. NS, not significant.

Example 9: Brief Treatment with GABBR1 Agonist Increases Long-Term Engraftment of Human UCB HSPCs Findings from the mouse model indicated a role for Gabbr1 neuroreceptor in two aspects of hematopoiesis: proliferation of HSPCs and differentiation of B lineage cells. To evaluate functional conservation of Gabbr1 in hematopoiesis, and translational potentials of GABA signaling for HSPCs, CD34$^+$ UCB cells were exposed for 2 hours in vitro with increasing doses of either baclofen (Bac), a clinically approved GABA agonist (Bowery, et al. (1980) *Nature* 283(5742):92-94), or 2-hydroxy-saclofen (Sac), a selective antagonist of GABA B receptor (Kerr, et al. (1988) *Neurosci. Lett.* 92(1):92-96). After treatment, cells were injected IV into sub-lethally irradiated NOD-scid.Il2rg$^{null}$ (NSG) recipients and xenograft outcome assayed 16 weeks later. Treatment with 10 µM Bac showed dramatic enhancement over vehicle control in engraftment of hCD45$^+$ cells in NSG recipients. At 16 weeks, CD45$^+$. (FIG. 1) and progenitor-specific CD34$^+$ (FIG. 2) BM engraftment in NSG mice exhibited a trend to increase after agonist treatment, and a significant improvement after a 10 µM Bac. Sac treatment did not significantly increase engraftment at any of the tested doses. Further lineage analysis of BM chimerism in vehicle control and 10 µM Bac treatment revealed significant increases in overall engraftment (CD45$^+$), and in progenitor engraftment (CD34$^+$ and CD38$^+$; FIG. 3). In the spleen of transplanted NSG mice, this pattern persisted with significant increases in overall engraftment, and a near two-fold enhancement in CD19$^+$ B-cell reconstitution (FIG. 4). At 16 weeks post-transplantation, CFU assays indicated that progenitor colonies in the BM derived from NSG mice transplanted with Bac-treated CD34+ UCB cells were three-fold higher than controls. Interestingly, CD34$^+$ UCB cells analyzed for in vitro CFUs after a 2-hour treatment, Bac did not produce increased colonies, indicating conditions in vivo are required for a sustained increase in progenitor numbers. This demonstrates that Gabbr1-mediated HSPC signaling promotes engraftment, reconstitution potential, and differentiation of the B cell lineage.

Example 10: Canonical GPCR Signal Transduction of GABBR1/2 in Hematopoietic Cells GABBR2 via G-alpha$_{i/o}$ proteins can inhibit adenylyl cyclase activity and lower cAMP levels. Downstream signaling through second messenger cAMP can be assayed ex vivo by loading BM nucleated hematopoietic cells with fluorescent cAMP analog, treating with agonist Baclofen, then validating the cAMP levels in GABBR1$^+$/GABBR2$^+$ double-positive HSPCs by intracellular flow cytometry. Using B cells isolated from wild-type and Gabbr1 null mouse BM via CD19$^+$ MicroBeads (Miltenyi Biotec), cAMP was quantified using a competitive ELISA Kit (Invitrogen). Notably, these cells were selected as they are a more abundant cell type than HSPCs and B cells also express GABBR1. This analysis indicated no significant decrease in acetylated cAMP levels in Gabbr1 null B cells compared to wild-type.

In addition, OP9 co-culture experiments were carried out to differentiate HSPCs in vitro toward B lineages. LSK progenitors (3,000-4,000 cells) were sorted from wild-type or Gabbr1 null mutants. These cells were plated on a stromal OP9 cells and induced to differentiate into B cells by supplementing media (a-MEM 25% HYCLONE™ FBS) with IL-7 (1 ng/mL) and Flt3L (5 ng/mL). At 12-14 days of culture, the hematopoietic cells that were in suspension were harvested, and cell counts and flow cytometric analysis gated on CD45$^+$ hematopoietic, CD11b$^+$ myeloid, and CD19$^+$ B cells were performed. Large numbers of B cell progenitors were robustly and reproducibly generated at day 12-14.

Figure 5:
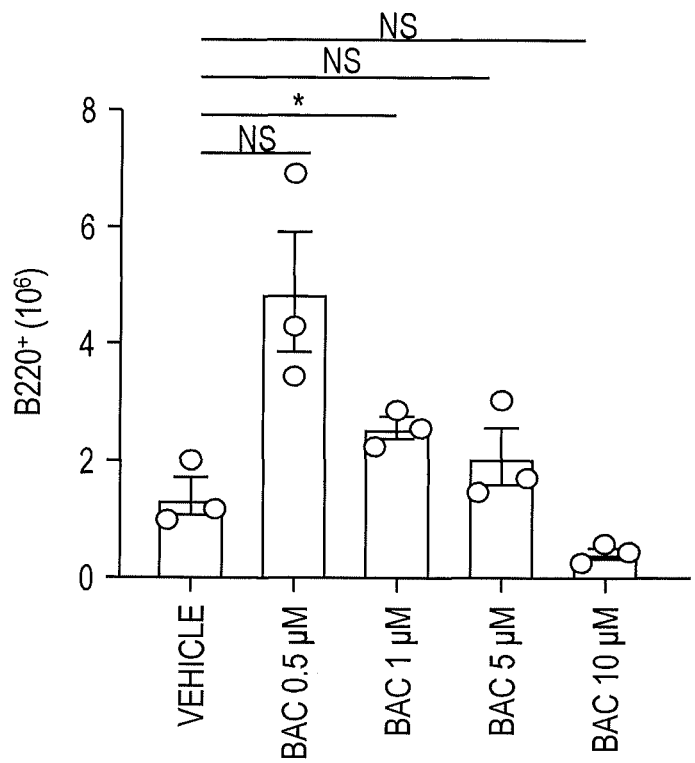
FIG. 5 shows a trend of B cell number increase, then decrease, with increasing doses of Baclofen ("Bac"). 1 µM Bac reached significance. A dose curve was used to test a range of responses (0.5, 1, 5, 10 µM Bac). B cell differentiation was analyzed in OP9 co-cultures at day 12. t-test: *p≤0.05. NS, not significant.

To test if OP9 co-cultures would respond to GABBR1 agonist during B cell differentiation, and allow downstream biochemical analysis, the co-cultures were treated with Baclofen. A dose curve was used to test a range of responses (0.5, 1.0, 5.0, 10 μM Baclofen). Cultures were harvested and analyzed for cell surface marker expression (B220$^+$ and GABBR1$^+$) by flow cytometry at day 12. A trend of B cell number increase, then decrease, with increasing doses of Baclofen agonist was observed, wherein only 1 μM Baclofen reached significance in its stimulation of B cell production (FIG. 5). These results are consistent with the model of GABBR1 stimulation regulating B cell production: GABBR1 agonist is stimulatory at low levels, but then inhibits production at high levels.

Figure 6:
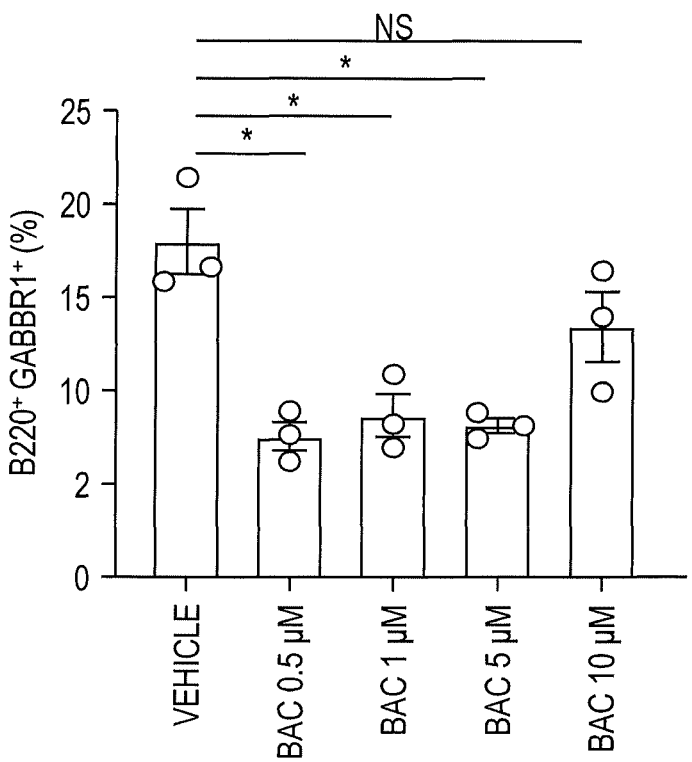
FIG. 6 shows the percentage of $B220^+$ cells that were also $GABBR1^+$ decreased with addition of Baclofen across a range of doses. A dose curve was used to test a range of responses (0.5, 1, 5, 10 µM Bac). B cell differentiation was analyzed in OP9 co-cultures at day 12. t-test: p≤0.05. NS, not significant.

As part of this self-regulating direct feedback mechanism, it was also determined whether there were any changes in GABBR1 surface expression in B lineages using flow cytometry. Although there is some debate about GABA B receptor endocytosis after sustained agonist exposure, there is evidence that GABA B receptors internalize after stimulation, desensitizing the cell, which leads to reduced inhibition of adenylyl cyclase. Using flow cytometry, it was observed that the percentage of B220$^+$ cells with surface expression of GABBR1$^+$ decreased with addition of Baclofen across a range of doses (FIG. 6).

Example 11: Requirement for BM GABA Production in B Cell Differentiation

To understand how differentiated progeny (B cells) signal to their stem and progenitor cells (HSPCs), the dynamics of the system needed to be measured in isolation. In hematopoiesis, the concept of stem cells whose fate decisions are regulated non-autonomously by receiving signals from progeny-derived factors has been proposed. Autonomous production of the GABA signal in the instant system needed to be measured during differentiation of B cells from HSPCs. Liquid chromatography-mass spectrometry (LC-MS) was used to measure GABA in the cell culture media of OP9 co-cultures. Using the AB/Sciex QTRAP® 5500 LC-MS with an Imtakt Intrada column and a run time of 18 minutes per sample, the system was optimized with the 87 m/z GABA reporter ion area under the curve (AUC) relative to the d6-GABA Internal Standard Calibration Method (ISTD) peak to do the quantitation. The r-value for that transition was 0.99878. After calibration with a GABA standard in DMEM media versus DMEM+FBS, it was determined that there was a low level of GABA present in FBS (~2.5 ng/ml), well below the levels produced in the experiment (>10 ng/ml). At days 3, 6, and 9 of differentiation when the percentage of CD19$^+$ B lineages in culture was still low, GABA concentrations were detected between 10-20 ng/ml above the DMEM/FBS control. Dramatically, when CD19$^+$ cells expanded at day 12, a more than 3-fold increase in GABA concentrations were detected in the co-culture media (~50 ng/mL).

To genetically block GABA production during B cell differentiation, the B lineage Cre lines CD79a/Mb1-Cre (19) and CD19-Cre were used (Rickert, et al. (1997) Nucl. Acids Res. 25(6):1317-8). These lines were crossed to a GAD1/2-floxed allele (Meng, et al. (2016) Proc. Natl. Acad. Sci. USA 113(13):3645-50) that also carries the Ai14 Lox-Stop-Lox-tdTomato Cre reporter (Madisen, et al. (2010) Nat. Neurosci. 13(1):133-40). At 6-8 weeks of age, BM were harvested and HSPCs (LSK) were sorted from GAD1/2$^{f/f}$; CD79a/Mb1-Cre (Cd79a KO) and GAD1/2$^{f/f}$-CD19-Cre (Cd19 KO) mice, as well as littermate Cre-negative controls (wild-type). GAD1/2$^{ff}$ excised by Cre recombination will delete the only enzymes that can produce GABA. HSPCs were plated, 3,000-4,000 per well, in OP9 co-culture and were differentiated for 12 days. Cells were harvested from co-cultures for analysis by flow cytometry. The Ai14 Cre reporter was used to confirm that >95% of CD19$^+$ and/or B220$^+$ cells were tdTomato$^+$ as an indication of robust Cre excision in B lineages. Removal of GAD1/2 with CD79a/Mb1-Cre, but not CD19-Cre, led to dramatic reduction of absolute numbers of CD45$^+$ hematopoietic and B220$^+$ B lineages. The percentage of B220$^+$ cells decreased with GAD1/2 deletion by CD79a/Mb1-Cre. Differentiation of Gabbr1 null HSPCs on OP9 co-cultures produced significantly less B cells. These results indicate that there is an early requirement for GAD1/2 enzymes and GABA production in the differentiation of B cells, as CD79a/Mb1-Cre is thought to be activated earlier in the lineage than CD19-Cre. Even more indicative of the mechanism is the fact that supplementing the media of these cells with Baclofen agonist partially rescues the defect due to GAD1/2 deletion.

Example 12: cAMP Assay for Determining GABA B Receptor Agonist Activity

The following procedure can be used to determine the level of intracellular cAMP. Recombinant HEK cells expressing the GABA$_B$ R1 receptor are used in the experiments. cAMP levels are measured using a cAMP XS$^+$ HitHunter™ Chemiluminescence Assay Kit (GE Healthcare Biosciences Corp.). Cells are seeded overnight at 5,000 cells per well, in black, clear bottom 96-well plates. The following morning, cells are washed twice with 100 μL PBS per well. Forskolin is weighed out and dissolved in DMSO to a final concentration of 100 mM. One-hundred μM forskolin solutions are prepared in PBS with and without a compound of interest at 1-times final concentration. Thirty (30) μL of the test solutions are added to the wells and incubated for 1 hour at room temperature. The cAMP concentration is determined according to the protocol described in the cAMP assay kit, maintaining the plate at room temperature and in the dark. Two hours after the final kit reagent is added, the plate bottom is covered with black tape, and the plate read using a microplate scintillation and luminescence counter (PerkinElmer, Waltham, MA). Each well is read for 6 seconds. The untransformed data are then analyzed.

What is claimed is:

1. A method for preparing hematopoietic stem and progenitor cells (HSPCs) for transplant into a subject in need thereof comprising treating the HSPCs ex vivo with an effective amount of a GABA B receptor (GABBR) modulator thereby preparing the HSPCs for transplant into the subject.

2. The method of claim 1, wherein the GABBR modulator comprises a GABBR1 agonist.

3. The method of claim 1, wherein the HSPCs are treated with the effective amount of the GABBR modulator for about one to about 16 hours.

4. The method of claim 1, wherein the effective amount of the GABBR modulator is about 1 nanomolar to about 50 micromolar.

5. The method of claim 1, wherein the HSPCs comprise CD34$^+$ HSPCs.

6. The method of claim 1, wherein the HSPCs comprise umbilical cord blood HSPCs.

7. The method of claim 2, wherein the GABBR1 agonist is baclofen.

8. The method of claim 7, wherein the effective amount of baclofen is about 10 micromolar.

9. The method of claim 8, wherein the HSPCs are treated for about 2 hours.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
caaaacagac aagtggatcg gagg              24

<210> SEQ ID NO 2
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 2
ctgggagttc tggatataac gaac              24

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 3 tcgattttc aaccagctct ctact              25

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 4
gtgcaatttc atatgtgaac atatt             25